United States Patent
Zumeris et al.

(10) Patent No.: US 7,892,191 B2
(45) Date of Patent: *Feb. 22, 2011

(54) NANOVIBRATION COATING PROCESS FOR MEDICAL DEVICES USING MULTI VIBRATION MODES OF A THIN PIEZO ELEMENT

(76) Inventors: Jona Zumeris, 15/4 Hatzivoni Street, Nesher 36831 (IL); Zadick Hazan, 5 Haganah Street, Zichron Yakov (IL); Yanina Zumeris, 15/4 Hatzivoni Street, Nesher 36831 (IL)

(*) Notice: Subject to any disclaimer, the term of this patent is extended or adjusted under 35 U.S.C. 154(b) by 775 days.

This patent is subject to a terminal disclaimer.

(21) Appl. No.: 11/131,314

(22) Filed: May 18, 2005

(65) Prior Publication Data
US 2005/0268921 A1    Dec. 8, 2005

Related U.S. Application Data

(60) Provisional application No. 60/572,650, filed on May 18, 2004.

(51) Int. Cl.
*A61B 17/22* (2006.01)
*A61N 7/00* (2006.01)

(52) U.S. Cl. .................. 601/46; 601/2; 601/47; 601/48; 601/84; 600/466; 600/467; 604/22; 604/266; 604/508; 427/565; 427/346; 606/169

(58) Field of Classification Search .............. 601/2, 601/46, 47, 48, 84, DIG. 4; 427/565, 346; 604/22, 508
See application file for complete search history.

(56) References Cited

U.S. PATENT DOCUMENTS

| | | | | |
|---|---|---|---|---|
| 4,698,058 A * | 10/1987 | Greenfeld et al. | ........... | 604/266 |
| 4,836,211 A * | 6/1989 | Sekino et al. | ................ | 600/461 |
| 4,961,424 A * | 10/1990 | Kubota et al. | .................. | 601/2 |
| 5,735,811 A * | 4/1998 | Brisken | ........................ | 604/22 |
| 5,904,659 A * | 5/1999 | Duarte et al. | .................. | 601/2 |
| 6,231,516 B1 * | 5/2001 | Keilman et al. | ............. | 600/485 |
| 6,428,491 B1 * | 8/2002 | Weiss | ............................ | 601/2 |
| 6,585,763 B1 * | 7/2003 | Keilman et al. | ............ | 623/1.42 |
| 2002/0103448 A1 * | 8/2002 | Babaev | ......................... | 601/2 |
| 2003/0153077 A1 * | 8/2003 | Pitt et al. | .................... | 435/383 |
| 2005/0038376 A1 * | 2/2005 | Zumeris et al. | ............... | 604/22 |

FOREIGN PATENT DOCUMENTS

WO    WO 03099100 A2 *  12/2003

* cited by examiner

*Primary Examiner*—Kevin C Sirmons
*Assistant Examiner*—Clinton Ostrup
(74) *Attorney, Agent, or Firm*—Malina & Associates, PLLC

(57) ABSTRACT

An apparatus and method is provided for preventing biofilm formation associated with an indwelling medical device. The method involves applying nanovibrational acoustic waves to surfaces of a medical device utilizing a piezo resonator to generate the waves.

29 Claims, 23 Drawing Sheets

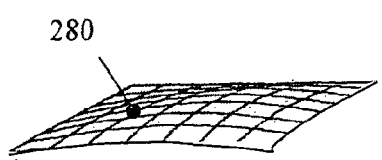
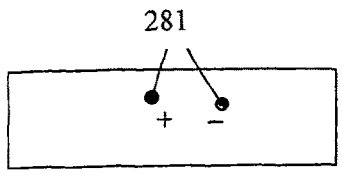
Fig. 13A Fig. 13B
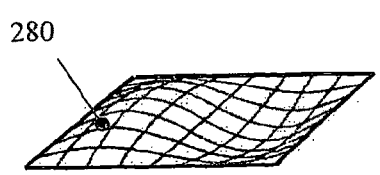
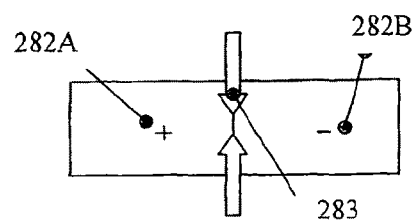
Fig. 14A Fig. 14B
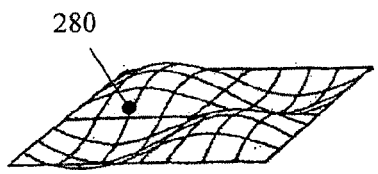
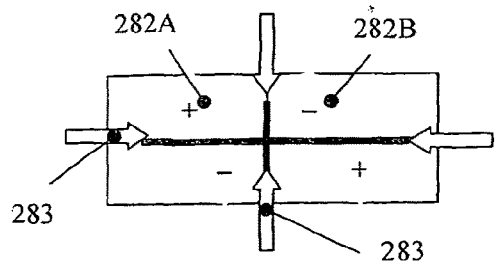
Fig. 15A Fig. 15B
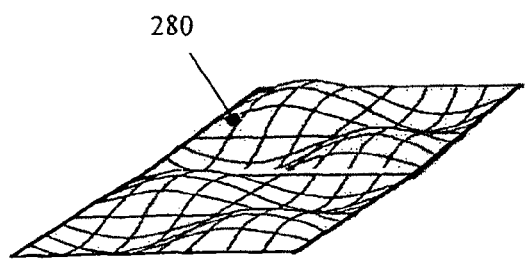
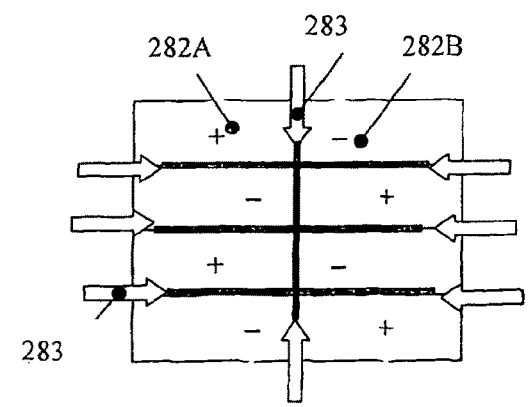
Fig. 16A Fig. 16B

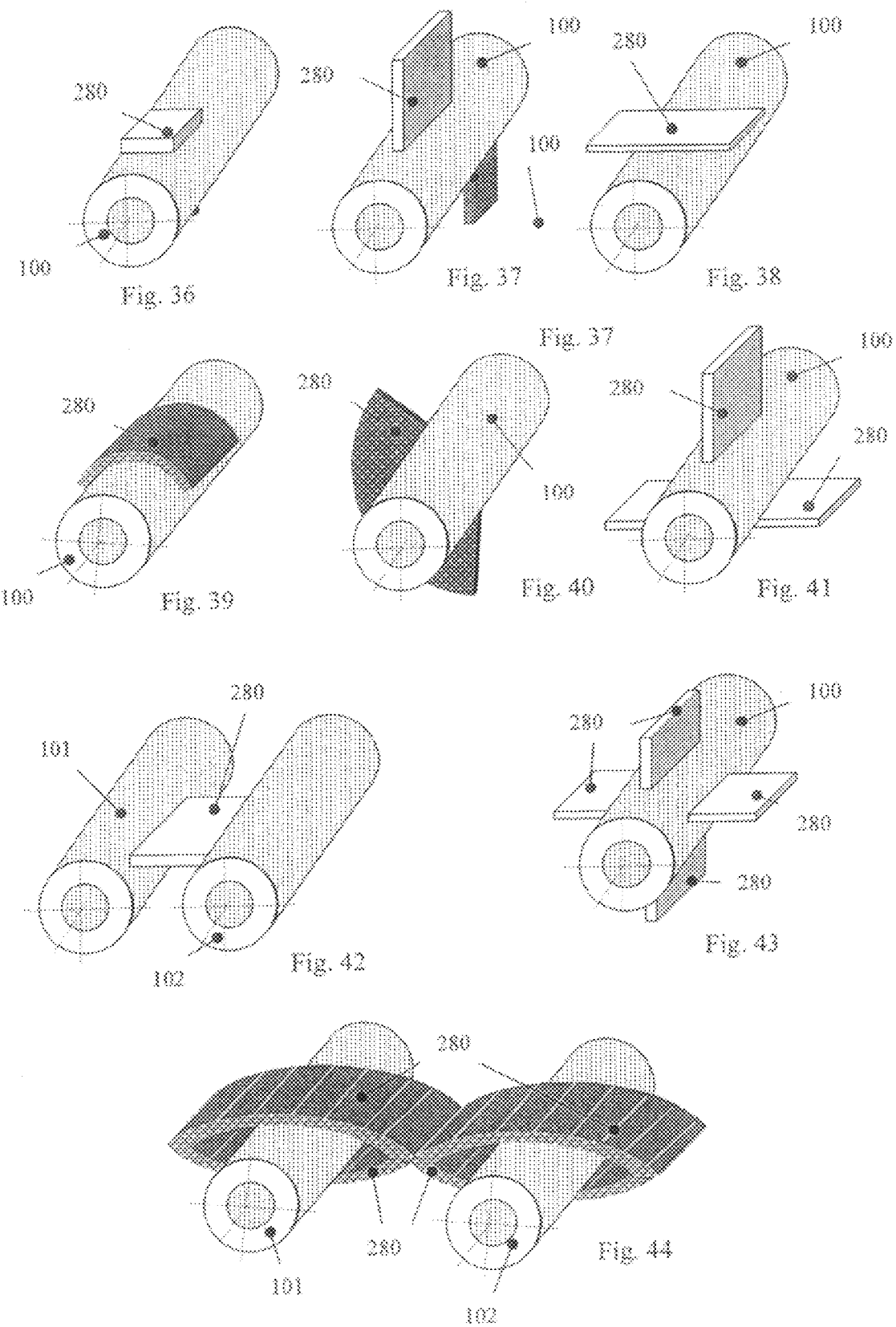

NANOVIBRATION COATING PROCESS FOR MEDICAL DEVICES USING MULTI VIBRATION MODES OF A THIN PIEZO ELEMENT

CROSS REFERENCES

This application claims priority from U.S. Application No. 60/572,650 filed May 18, 2004.

FIELD OF THE INVENTION

This invention relates generally to indwelling medical devices such as stents, catheters, tubes and other accessories that remain in a living body for protracted periods and are associated with bacterial contaminations and biocompatibility problems. The invention relates more particularly to systems for keeping the surfaces free of undesirable microorganisms and contaminating debris. An "indwelling" device is one that is emplaced and left for protracted periods, such as fifteen minutes or longer.

The invention is applicable to urinary catheters, tracheal, cardiac, central or other venous catheters, implants and other medical accessories. The invention is also suitable for use with tubes that irrigate or drain body cavities such as (without exclusion) for pleural, peritoneal, and intra tracheal cavities.

THE RELATED ART

The present invention primarily addresses problems that arise from accumulation of clogging deposits and contaminating bacteria on an indwelling catheter or other implants. More particularly, the present invention relates to problems of formation, multiplication and migration of microorganisms and contaminants on indwelling medical devices and especially on catheter surfaces.

Bacterial biofilm formation on medical devices (catheters, feeding tubes, endotracheal tubes, intravenous lines, etc.) is known to be a major source of hospital-acquired infection. The formation of biofilm on implanted devices such as urinary catheters, endotracheal tubes, gastrostomy feeding tubes, and intravenous lines indicates the presence of bacteria which are a leading cause of hospital-associated infections. These infections often cause serious complications and lead to increases in mortality, hospital stays and medical costs. Researchers from the Medical College of Virginia have, in *Emerging Infectious Diseases*, Vol. 7, No. 2, March-April 2001, conservatively estimated that between 875,000 and 3.5 million people acquire nosocomial infections annually in U.S. hospitals.

Over the last few years, it has become clear that about 80% of all bacterial infections are due to the formation of bacterial communities organized in a matrix of their own production. The matrix confers resistance to antibiotics and inhibits clearance by the immune system. In order to establish such communities, the bacteria communicate with one another via chemical signals. The first step of biofilm formation on the surface of medical devices starts with the attachment of bacteria to the surface. Following thereafter is communication between the members of the community, known as quorum sensing. Since this process is dependent upon the attachment, it is clear therefore, that by preventing attachment, one can prevent the cascade of biofilm formation.

Biofilms resistance has huge impact on health and medical care cost. Various solutions are offered, such as coating devices with silver ions or antibiotics. These solutions are short lived; the elution of antibiotic or silver ions is stopped by mucosal secretion and coagulated debris. Some literature reports that ultrasonic treatment of biofilms enhances the effectiveness of antibiotics.

The prevention or removal of accretion by attaching conventional ultrasound transducers to a medical device is described by Qian, Sagers and Pitt in *The Role of Insonation Intensity in Acoustic Enhanced Antibiotic Treatment of Bacterial Biofilms, Colloids Surfaces B: Bacteriol* 1994; 176; 2773-2780. Commercially available transducers by definition provide only one vibration form at a time: longitudinal or torsion, or bending. Conventional transducers are bulky, expensive and limiting. Their attachment to medical devices is very complicated. They are designed to create volume vibrations (in addition to surface vibrations), which demands high amounts of energy. The energy is wasted in the form of heat within the mass of the device. To date, the methods of combating this source of serious medical complications with their prohibitive economic impact have proved less than satisfactory. A major hindrance to wider use of indwelling devices is the inherent risk of infections associated with their use. The reduction of the risk is expected to open a whole new range of possibilities and the use of the technology in virtually all indwelling devices.

SUMMARY OF THE INVENTION

The formation of bacterial communities on surfaces, such as medical devices, is dependent upon communication between the members of the community. This communication is effected through chemical molecules generated by the micro organisms. These should be viewed as an active biological process.

Nanovibrations transmitted and propagated on the surfaces of medical devices and in proximity thereof interfere with the biological process. The result is that less extracellular matrix characteristic to these communities, known as biofilm, is produced. The extracellular matrix is composed mainly of polysaccharides which make bacteria resistant to immune system and to antibiotics and disinfectants.

Our technology concept is based on surface acoustic waves (SAW). Extensive experiments in our laboratories show that through surface acoustic waves (SAW), particularly, nanovibrations, we can achieve prevention of the bacteria attachment because the microorganisms do not have a film surface to attach to.

Surface acoustic waves (both Rayleigh and pseudo SAW) can be generated at the free surface of an elastic solid (medical device). Let us consider the propagation of a Rayleigh wave on an elastic surface, which may be associated mechanically with time-dependent elliptical displacement of the surface structure. One component of this physical displacement is parallel to the SAW propagation axis, while the other is normal to the surface. Distance x relates to the SAW propagation axis, while y is a normal axis in a coordinate system. The amplitude of surface displacement along the y-axis is larger than along the SAW propagation axis x. The amplitudes of both of these SAW displacement components become negligible for penetration depths greater than a few acoustic wavelengths into a body of the solid. Pressure (gas or fluid loading) contributes to acoustic wave attenuation and velocity change. The attenuation is due to the generation of compressional waves in the gas or fluid in contact with the surface applying SAW. In other words, the shear vertical component of the wave causes periodic compression and rarefaction of the gas or fluid, resulting in a coupling of acoustic energy from the devices into the gas or fluid. Attenuation varies linearly with acoustic pressure. In the case of a urinary catheter, where biofilm is formed both on external and internal surfaces, it is desirable to have SAW distribution uniformly on both surfaces. The proposed invention utilizes a thin piezo element as a resonator for the generation and distribution of SAW. This resonator offers the following advantages:

1. Low energy requirement enabling extended use of light weight batteries;
2. The piezo element being lighter and smaller facilitates the coupling to existing medical devices without requirement of extra space, and therefore no major modifications to standard medical devices are necessary;
3. These elements are economical and will be disposed at the end of their use;
4. The miniature size of the proposed piezo element does not compromise the flexibility of medical devices;
5. The miniature size of the proposed piezo element enables use of one or more elements in the same device and facilitates their mass production.

Extensive experiments in our laboratories show that through surface nanovibrations, we can achieve interference with the bacterial growth problem. The microorganisms do not have a film surface to attach to the above described cycle, so cannot propagate and this cycle is disrupted. The effect is extended to surrounding areas for several centimeters and biofilm is prevented, not only on the device, but also the adjacent tissues. Vibration wave length and acoustical energy are determinant factors in achieving the anti-microorganism effect. A virtual nanovibration coating is established on the surface of accretion matter as well as on the clean surface. Sometimes accretion takes place when high concentrations of particulate matter are present (which results in a high viscosity, sticky substance). The device becomes coated with the layers of particulate matter. In such circumstances, the establishment of accretion does not inhibit the nano vibrated coating to be established effectively upon the surface of the accretion matter.

Furthermore, the proposed invention is related to biomaterials and biocompatibility. Biomaterial is defined as a natural or synthetic substance used in the treatment of a patient that interfaces with tissue at some stage and is related to complications. Researchers consider that it is essential to optimize biocompatibility and decrease biomaterial related complications such as infection and encrustation within urinary tract, vascular lines, and those associated with implants. The process of precipitation and formation of crystals is accelerated kinetically by the presence of rough surfaces, catheter holes and edges. The proposed invention by generating surface acoustic waves excites vibration of the material structure resulting in a decrease of friction of the biomaterial. This phenomenon improves biocompatibility by reducing frictional irritation and cell adhesion at the biomaterial-tissue interface.

In addition, it was found that ultrasound has an effect on antibiotic activity and less antibiotic is needed for the desired result to obtain. That is why the generation of SAW on implant or indwelling medical device surfaces will activate antibiotic action. The proposed invention applying of SAW to medical devices opens opportunity to decrease friction, decrease antibiotic use and increase efficiency of drugs used with indwelling medical devices. These are important tools for biomaterials biocompatibility and decrease of biomaterial related complications such as infection and encrustation.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting wherein:

FIGS. 13A, 14A, 15A and 16A are graphical illustrations of the normal modes of a rectangular plate;

FIGS. 13B, 14B, 15B and 16B are schematic illustrations of the same modes for different n and m harmonics;

FIGS. 36-44 are schematic illustrations of proposed attachments of the resonators to a medical device or parts thereof (the proposed examples may be applicable while integrating piezo resonator to new medical devices. One or more SAW process resonators may be attached to single medical device);

DETAILED DESCRIPTION OF THE DRAWINGS

Figure 1:
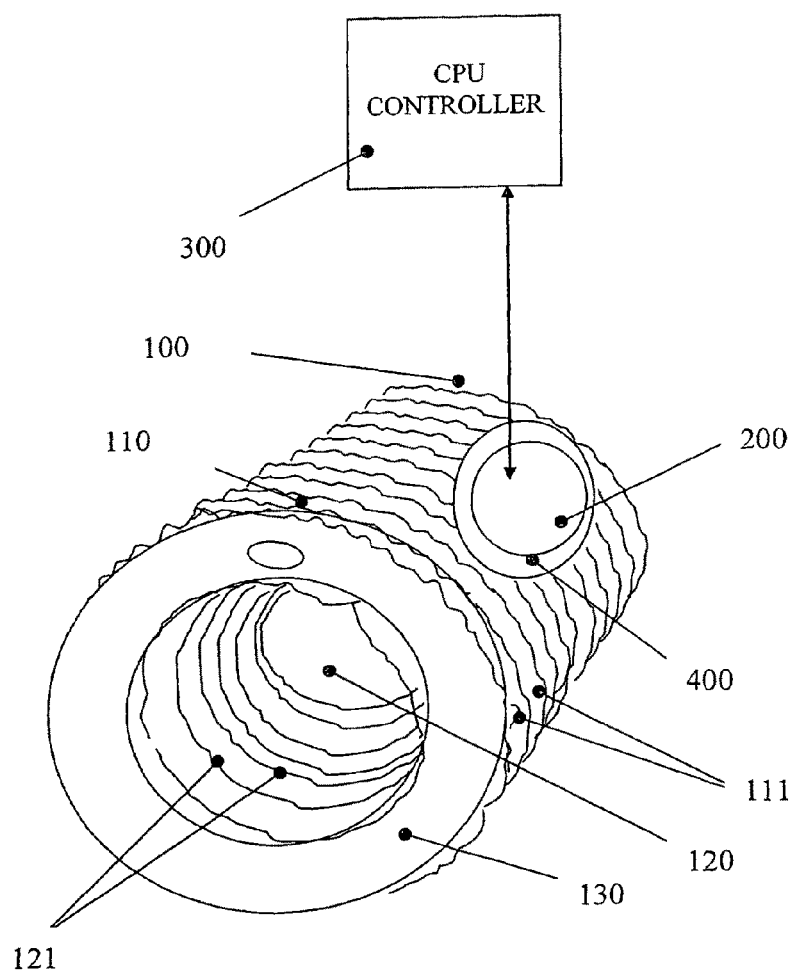
FIG. 1 is a schematic illustration of a thin mechanical vibration element and a switching device for propagation of elastic acoustic longitudinal waves in a medical device system for nanovibration coating of the external and internal surfaces for preventing biofilm formation and/or dispersing biofilm formations, where the thin piezoelectric ceramic have at least one shape of electrodes on the internal and external surfaces, according to some embodiments of the present invention.

FIG. 1 illustrates an embodiment of the invention including an indwelling medical device 100, which has a passageway for fluids, liquids, gases, or both. The liquids can flow into and out of the patient's body. The indwelling medical device may have standard or specially designed configuration.

The target of the invention is to prevent biofilm formation on external 110, internal 120 and end surfaces 130 of the medical device 100. This target is achieved by exciting acoustic waves in nanometer range on the surfaces of the medical device (SAW). The process may be considered as a virtual nanovibration coating process. A main feature of this process is that every material point of the surface is moving and there is no point which is not moving at least in one place. The process comprises ability to form SAW on external, internal, torsion surfaces and the binding lines between them—simultaneously or separately.

Furthermore, this small mechanical vibration energy transferred to the surface of medical device inhibits bacteria attachment and prevents entry of microorganisms from external and internal sources.

To generate nanovibration coating process on the inside and outside surfaces of the medical device, the actuator-resonator of mechanical vibrations should be attached to the medical device. The resonator 200 should be coupled on the medical device outside of the patient's body.

A series of experiments have proved that resonators based on reverse piezo effect principles are most suitable and show the best results. Piezo resonator 200 is capable of generating high frequency mechanical vibrations, in the range from KHz to MHz. These high frequency mechanical oscillations of the resonator 200 create surface acoustic waves (SAW) with wave lengths less than 100 micron. The amplitudes of these vibrations are of several nanometers.

The type of SAW excited on the internal 121 and external 111 surfaces of the medical device 100 features running wave character. The waves are transmitted in two opposite directions from the resonator 200. The controlled SAW process (nanovibration coating process) achieves the effect of pushing or pulling materials on said surfaces, including fluids and particulates suspended in them. In the case of biofilm developing both independently or dependently of the medical device, the introduction of nanovibration waves will: (a) reduce the existing biofilm; (b) will augment and enhance the effect of antibiotics on the biofilm (decrease the biofilm resistance to antibiotics) producing antimicrobial and antithrombogenic surfaces.

When resonator 200 utilizes a thin PZT plate element, a periodical rectangular electrical pulse is applied from the driver and the thin PZT plate element mechanically vibrates in normal vibration modes. It must be emphasized that energy consumption required to excite these vibrations is low (in comparison to other methods) and the process can be extended for a long period of time. Experiments have proved the ability to prevent biofilm formation on the surface of medical devices for the time period up to 28 days.

Thin plate type piezo resonator 200 may require different shapes dependent upon the type of medical device and operating conditions. The main shapes for thin piezo plate resonators are those selected from a plate, disk, membranes (plates and disks), thin membrane shells, and their combinations.

As is shown in FIG. 1, thin piezo resonator 200 is electrically coupled to CPU controller 300. The frequency of the electrical oscillator is in direct relationship to the frequency of generated mechanical oscillations in the resonator 200. The energy source applied may have periodical or non-periodical character and may be of electromechanical or electro-magnetical nature.

Furthermore, to increase the efficiency of transmission of the mechanical vibrations from resonator 200 to the surface of the medical device 100, a special coupling system 400 should be applied. System 400 consists of matching layers having different thicknesses and is dependent on materials and composites. The coupling system 400 operates to minimize self-heating in the resonator. For optimal process, the resonator is adjusted to work in a resonance with SAW process on internal, external and end surfaces of medical device.

Figure 2:
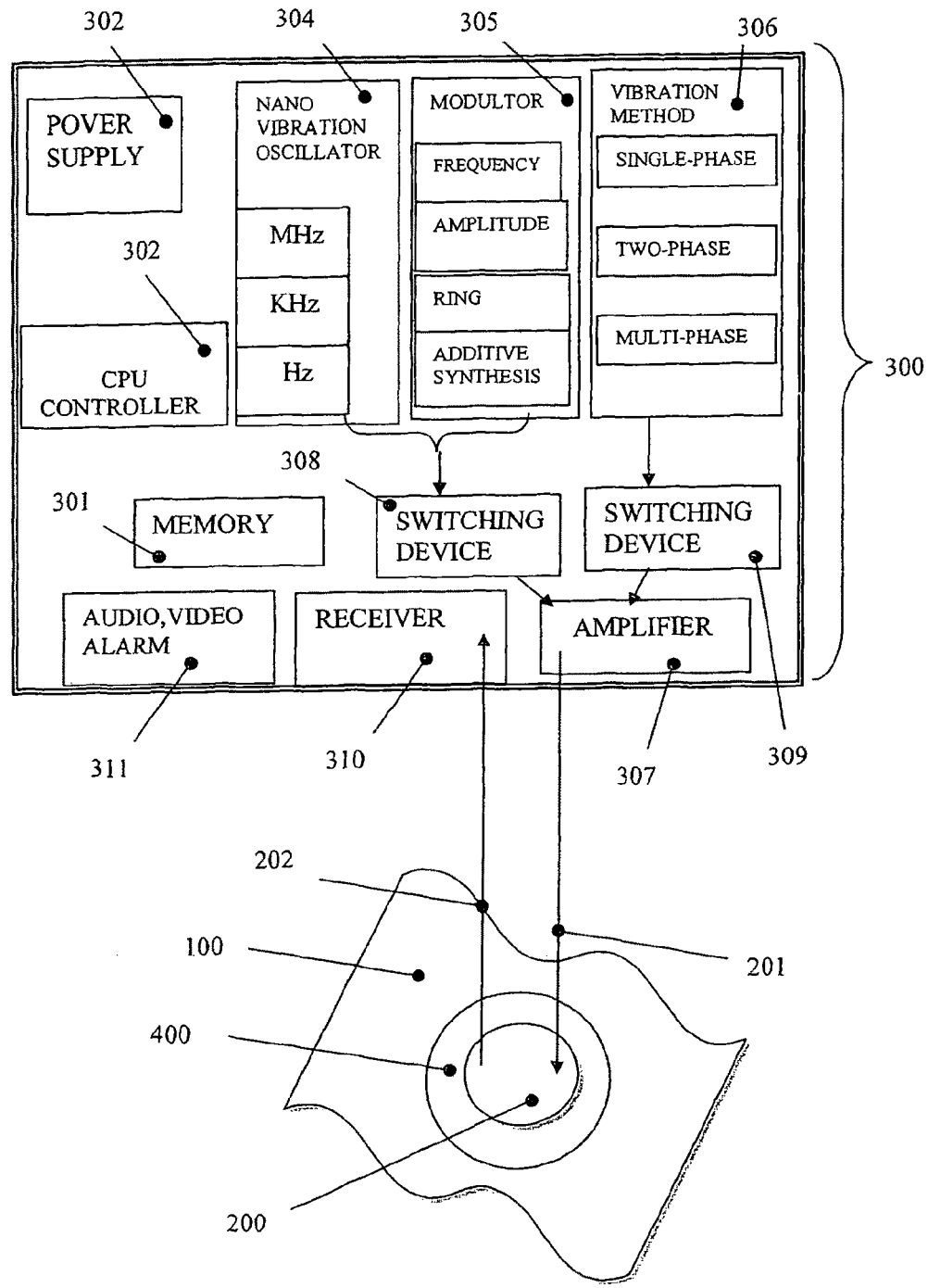
FIG. 2 is a schematic illustration of a thin mechanical vibration element and a switching device for propagation of elastic acoustic longitudinal waves in a medical device system for nanovibration coating of the external and internal surfaces for preventing biofilm formation and/or dispersing biofilm formations, wherein the thin piezoelectric ceramic have at least one shape of electrodes on the internal and external surfaces according to some embodiments of the present invention.

FIG. 2 illustrates the acoustic medical device system which includes a central processor unit (CPU) and a thin piezo plate resonator 200 as an electromechanical converter. Plate 200 is directly or through coupling system 400 attached to an ordinary or specially designed medical device 100 or part thereof CPU 300 transmits and controls electrical signals applied to the thin piezo electromechanical resonator 200. The resonator 200 converts electrical signals from CPU 300 to mechanical energy proportionally in respect to time and range. As a result, thin resonator 200 is excited to mechanically vibrate, and its mechanical vibration space vectors have a changeable character. One or more such resonator (actuator) 200 may generate surface mechanical vibrations on medical device 100. The occurrence of SAW on the medical device depends on the particular area to which the resonator 200 is attached. SAW may be considered as a virtual nanovibration coating on all the surfaces of actual medical device 100. Thin piezo resonator 200 transmits generated mechanical vibration energy to the medical device 100. On the other hand, the resonator is capable of controlling this process by transmitting to the CPU electrical signals proportional to a maximum mechanical energy range on the medical device (for maintaining safety requirements). For these reasons, the proposed electronic block of CPU 300 should have appropriate data input for the type of geometrical size of the medical device. This information is registered in memory block 301.

Electronic block of CPU 300 includes power supply 302 (battery or alternating current), memory 301, controller 303, nanovibration oscillator 304, modulator 305, vibration method controller 306, device for applying vibration method amplifier 307, switching devices 308 and 309, receiver 310 and audio-video alarm device 311. CPU 300 is connected electrically with mechanical vibration resonator 200 by forward and backward connections 201 and 202. Nanovibration process on the surface of the medical device occurs when every point of the surface moves in the range of nanometers. Resonator 200 sourced with electrical signals from CPU 300 simultaneously produces various frequencies (resonance and non-resonance) of mechanical vibrations. The properties to produce vibrations in different frequency resonances simultaneously are characteristic to materials with piezoelectric features. The more detailed discussion which follows assumes that mechanical vibration resonator 200 is manufactured in a shape of a thin piezo plate and has two or more electrodes.

Figure 3A:
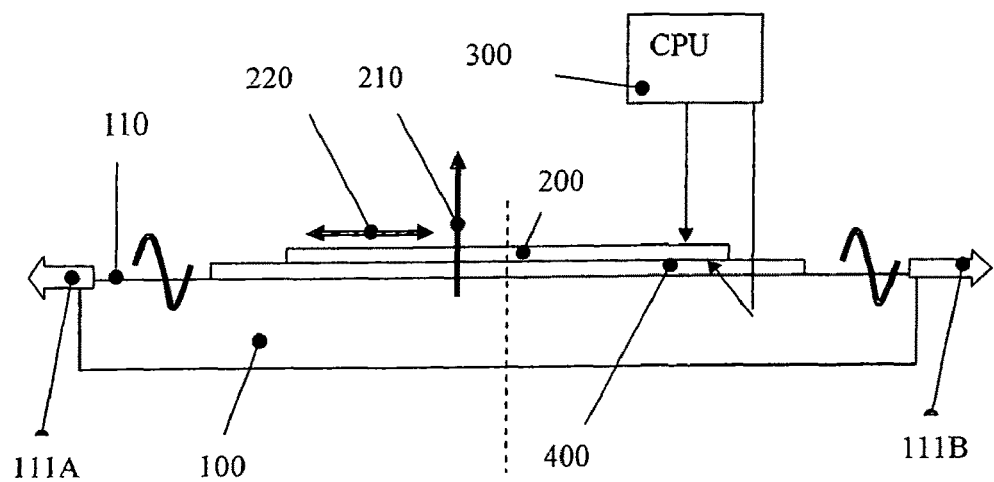
FIGS. 3A-3B are schematic illustrations of the direction of surface acoustic waves on an external medical device surface when longitudinal vibration modes of a thin piezo element are applied.
Figure 3B:
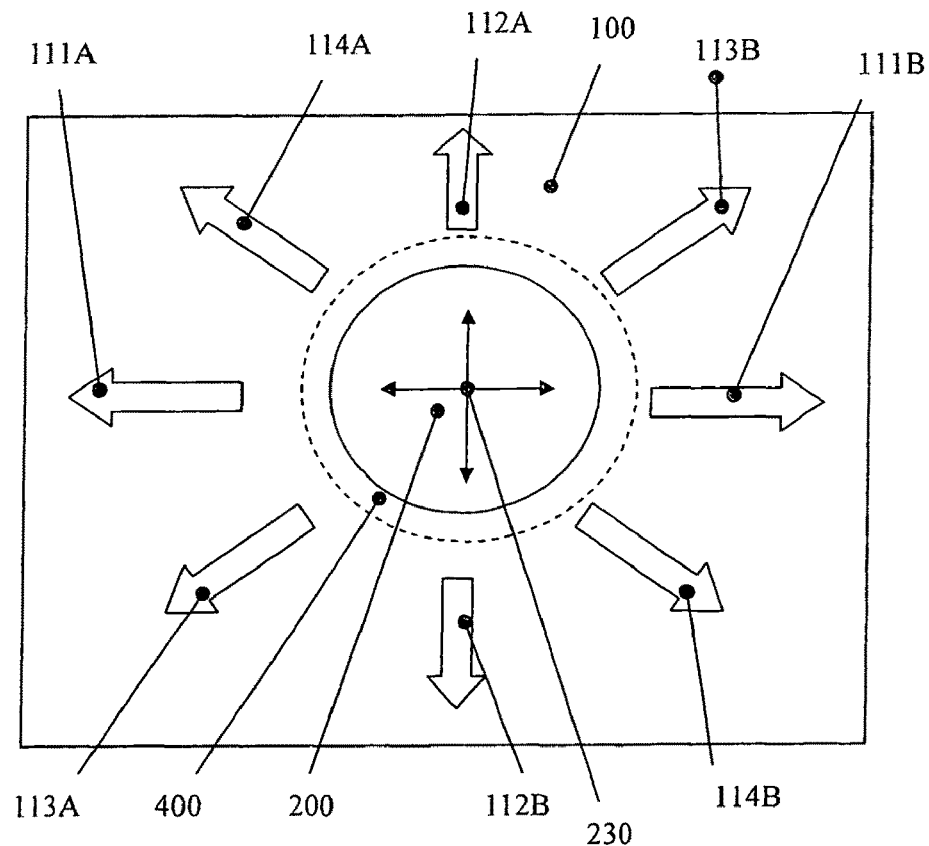

FIGS. 3A and 3B illustrate such type thin piezo resonator 200 (disk shape) coupled through matching system 400 to external surface 110 of the medical device 100. Resonator 200 is coated with electrodes (silver, brass, gold, or other) with electrical conductors for transmission of electrical signal from CPU 300. Each thin piezo resonator 200 surface electrode may have one or more isolating zones of different area. Alternatively, thin piezo resonator 200 may have simple or multiple direction polarization of the piezo material.

FIGS. 3A and 3B also show the thin piezo resonator (disk shape) 200 with thickness polarization 210. Thin piezo resonator 200 can be manufactured so as to mechanically vibrate in thickness and other modes such as longitudinal, radial and bending, separately or simultaneously.

Figure 4:
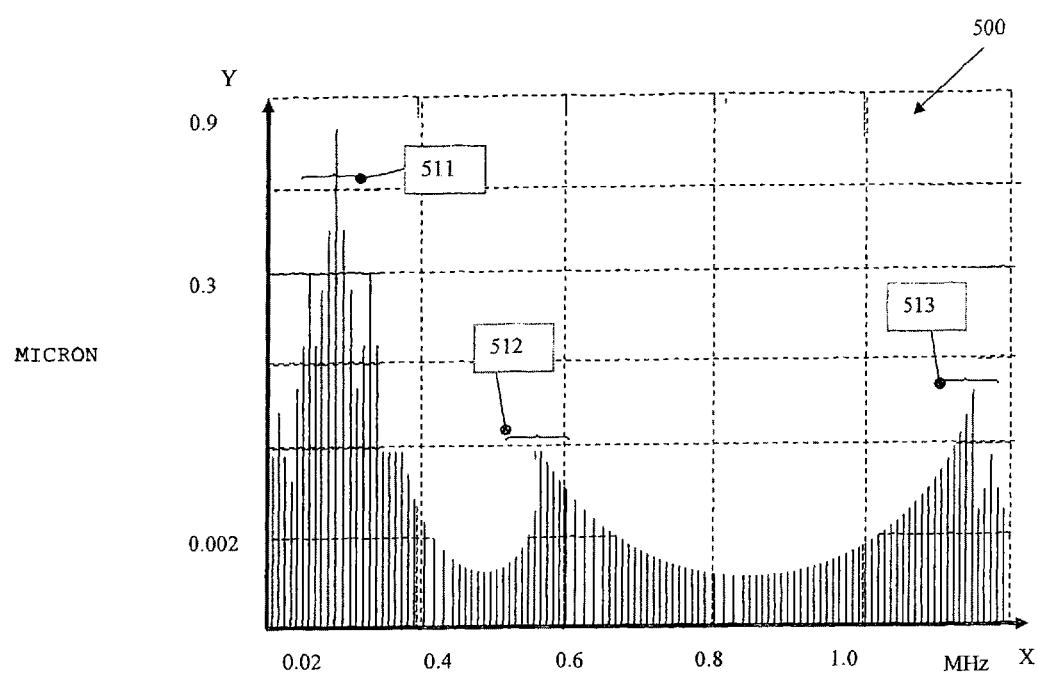
FIG. 4 is a schematic illustration of a spectrum plot of SAW across a medical device, while longitudinal self vibration mode of a thin piezo element is being applied for preventing biofilm formation and/or dispersing biofilm formations, according to some embodiments of the present invention.

FIG. 4 illustrates the spectrum diagram 500 of mechanical vibration amplitudes versus frequency. For example, thin piezoceramic device 200 may vibrate in bending mode (frequency spectrum zone 511) and simultaneously vibrate in other modes—radial vibration mode (frequency spectrum zone 512) and thickness mode (frequency spectrum zone 513). On the other hand, one vibration mode (for example radial) may cause other vibration modes (thickness, bending). This feature depends on thin piezo element shape and geometrical sizes, polarization direction, technical characteristics of piezo material, quality factors, and so on. The number of vibration modes depends on the form of electrical signal applied to the thin piezo element, which may be periodical, pulse, or special wave form. Application of a pulsed electrical signal may not only generate main but also subsequent harmonic vibrations. When the relation between thin piezo element thickness and length is no less than 1:10, the additional frequency harmonics occur. This may result from internal friction of piezo material particles applying large amplitudes. Tenths of microns vibration amplitudes create strong non-linear processes. Application of a wide spectrum of frequencies to the thin piezo element simultaneously excites the element to vibrate in multi vibration modes. The wide spectrum of vibration modes of piezo resonator enables generation of SAW on the surface of different parts of the medical device. They may be manufactured of different materials and have different acoustic velocities and SAW wave lengths. The meaning of SAW process is that each point of the surface of medical device is moving in a three dimensional scale range and this process can be understood as virtual nanovibration coating of the surface.

Thin piezo resonator 200 produces a wide range of diapason mechanical vibrations: from several Hz to MHz. FIG. 2 shows an electrical drive CPU 300, which varies the shape and time of the electrical signal. Nanovibration oscillator 304 may generate separately or simultaneously electrical signals in the range of Hz, KHz, or MHz These impulses may have harmonic, impulse, or special wave forms, featuring harmonic and non-harmonic vibrations.

For widening the spectrum of signal frequency, as it is shown in FIG. 2, vibration oscillator 304 through switching device 309 (which is controlled by controller 302) is connected to modulator 305. Modulator 305 has an electronic block which allows to conduct, separately or simultaneously, modulation of amplitude (AM), modulation of frequency (FM), ring modulation (RM), additive, subtractive, gradual and wave table synthesis. The synthesized signal from modulator 305 enters the vibration mode device 306, which in response to controller 302 command, converts the signal to single phase, two phases, or multi phase signal. The signal through amplifier 307 and second switching device 309 is conveyed to different spaces of mechanical vibration excitement on thin mechanical vibration resonator 200 (for thin piezo element in FIG. 3 such spaces are different electrodes). Sound or optical alarm system 311 controls and signals if the system is operating/not operating (for example, if a bad contact occurs). The option exists to control and adjust in relation to patient health status and to match biological cycles, changes in body temperature, or pathological conditions. Such alarm system is utilized in the "Uroshield" device designed by Nanovibronix, Ltd., and it informs the user about low battery power or non contact of wires. Alternatively, the alarm system may inform about interferences (for example, caused by the motions of the patient) of the controller, and prevention of the situation by a corresponding command. In other words, the sensing function of the medical device can activate changes in vibrations of the system and continuation of biofilm preventing process. The sensing ability may compensate for interferences of the part of the medical device inside the patient body. If it is needed, the sensing may give information on blood flow pulsation. Mechanical vibration resonator 200 has its natural vibration frequency spectrum which depends on medical device 100 material, shape, the place of attachment of resonator 200, and coupling system 400. The range of frequency of the mechanical vibration resonator 200 may vary between about 1.0 Hz and about 50 MHz. The feedback enables control of vibration modes and their harmonics of self SAW process. SAW has running wave character and is adjusted to elastic characteristics of material constituting the resonator device.

FIG. 3A shows two directions of SAW-111A and 111B-on the external surface 110 of medical device 100. Thin piezo element 200 is attached through the coupling system 400 to external surface 110 of the medical device 100. Piezo plate resonator 200 vibrates in a longitudinal mode 220 (polarization direction—thickness 210), generates two SAWs, running in opposite 111A and 111B directions from piezo plate resonator 200. Experiments by Nanovibronix, Ltd. have shown that SAW maximum amplitude is generated, when relation between thickness and length of plate is 1:8.

FIG. 3B shows the appliance of disk shape piezo plate resonator 200, which vibrates in radial vibration mode 220. The SAW generated on the surface of the medical device due to disk shape, will have the following directions: 111A-111B, 112A-112B, 113A-113B, 114A-114B. Applying disk shape thin piezo element resonator 200 for SAW, it is possible to generate homogeneous vibrations in all radial directions of SAW (that is impossible with other shapes). The method described is applicable when SAW is desired for biofilm prevention on external surface 110 of medical device. In practice, often it is necessary that the vibration processes are applied to the internal surfaces. On the other hand, the internal surfaces may be difficult to reach, very small, or have other qualities not allowing attachment of the resonator directly to these surfaces.

Figure 5:
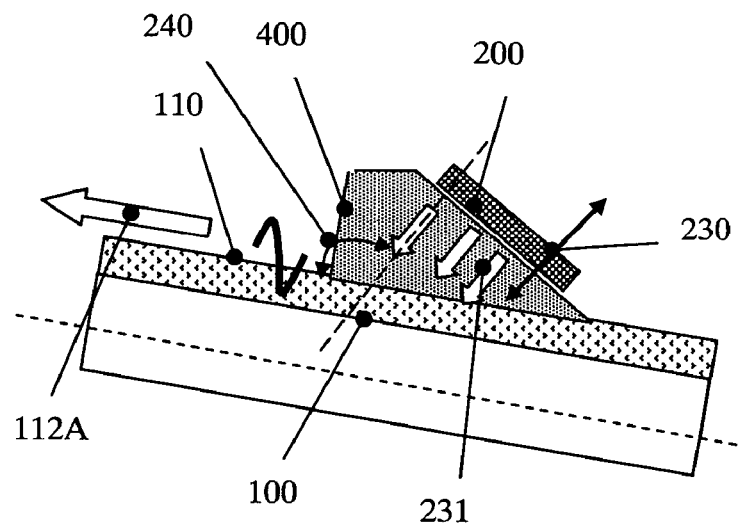
FIG. 5 is a schematic illustration of SAW directions using thickness vibration modes of a thin piezo element.

The method below describes SAW generation in one predetermined direction by means of a resonator attached or integrated to the external surface of the medical device. FIG. 5 illustrates a thin piezo resonator 200 attached through a special prism shape of matching layer (coupling system 400) to the external surface 110. The resonator 200 mechanically vibrates in thickness mode 230 and through coupling system 400 transmits directed mechanical energy. Mechanical energy in the form of flat longitudinal wave 210 is transmitted (with the angle 240) to a zone between external surface and coupling system surface. The angle 240 is chosen to match the acoustic velocity in the coupling system and to be higher than acoustic velocity on the external surface 110 of the medical device 100. On the other hand, the acoustic velocity of thin piezo resonator 200 should be higher than the acoustic velocity in the coupling system 400. The result is that between the external surface 110 of the medical device and coupling system 400, the SAW process is excited. SAW is operative when periodical mechanical vibration energy in the form of longitudinal wave 231 has the space period of the wave length equal to the wave length of the SAW on the medical device. The direction 112A of mechanical oscillation 231 is positive with respect to resonator 200.

Figure 6:
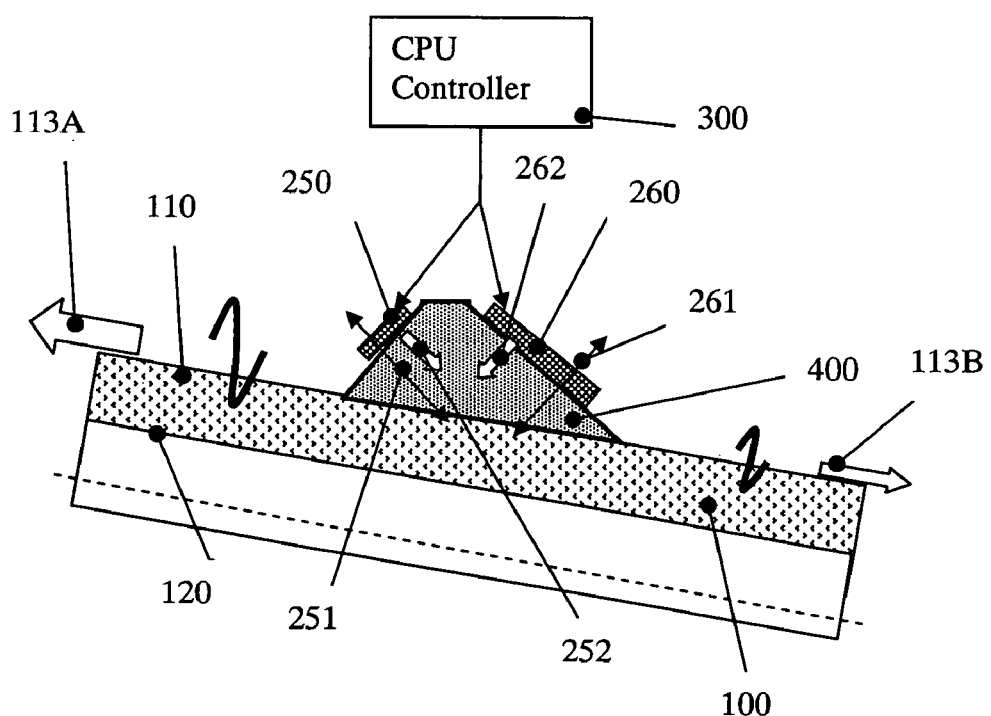
FIG. 6 is a schematic illustration of SAW process when in respect to resonator this process is stronger in a positive direction than in an opposite direction (two thin piezo element resonators are attached to the coupling system and resonator vibrates in thickness mode)

FIG. 6 illustrates ability to develop SAW (virtual nanovibration coating process) on entire external device surface 110. The SAW process with respect to the resonator is stronger in positive direction 113A than in opposite direction 113B. This may be achieved with prism shape coupling system 400. Two thin piezo element resonators 250 and 260 are attached to the coupling system. The resonator 250 vibrates in thickness mode 251 and generates mechanical oscillation energy, which in the form of longitudinal wave 252 through coupling system 400 transmits mechanical energy to the zone between the coupling system and medical device surface. This energy contributes SAW in the negative direction 113B with respect to the resonator. The conditions for SAW development have been described above through FIG. 5. Similarly, mechanical energy in longitudinal wave form on the zone between the coupling system and medical device surface 110 through coupling system 400 may be generated by thickness vibration mode 261 of thin piezo element 260. The CPU 300 controls the parameters (frequency, amplitude, signal form, duty cycle and other) of thin piezo elements 250 and 260. These are vibrating respectively in thickness 251 and thickness 261 mode. FIGS. 5 and 6 explain the method of generating SAW (virtual nanovibration coating process) on external medical device surface. Analogically SAW may be excited on the internal medical device surface with the thin piezo resonator attached to internal surfaces 120 of the device. The appropriate SAW should be chosen with respect to the biological problem. A stronger SAW level ordinarily is necessary for internal surfaces of the device and weaker levels for the external surfaces of indwelling medical device, as per FDA requirements for acoustic energy. Short term strong SAW levels may be desired as prophylactic means for biofilm prevention on implants thereby creating antimicrobial and antithrombogenic effects.

On the other hand, a majority of medical devices require prevention of biofilms all over the surfaces of the device. From this point of view, it may be desired to arrange virtual nanovibration coating process on all the surfaces by means of one thin piezo element. Attaching a thin piezo element having its polarization axes perpendicular to the medical device surface and applying longitudinal vibration mode of the piezo element results in SAW process on the external surface only. Analogously, using thickness vibration mode of piezo element directs SAW onto the internal surface only.

Both external and internal surface nanovibration coating can be accomplished through applying the bending mode vibrations of the piezo element to these surfaces. SAW is created when the bending vibration mode period is equal to the length of the surface acoustic wave. By actuating in different variations (either directly or through piezo element) controlled various combinations of vibration modes, which can be created simultaneously and changed periodically, all vibration modes may be achieved with one element.

Figure 7:
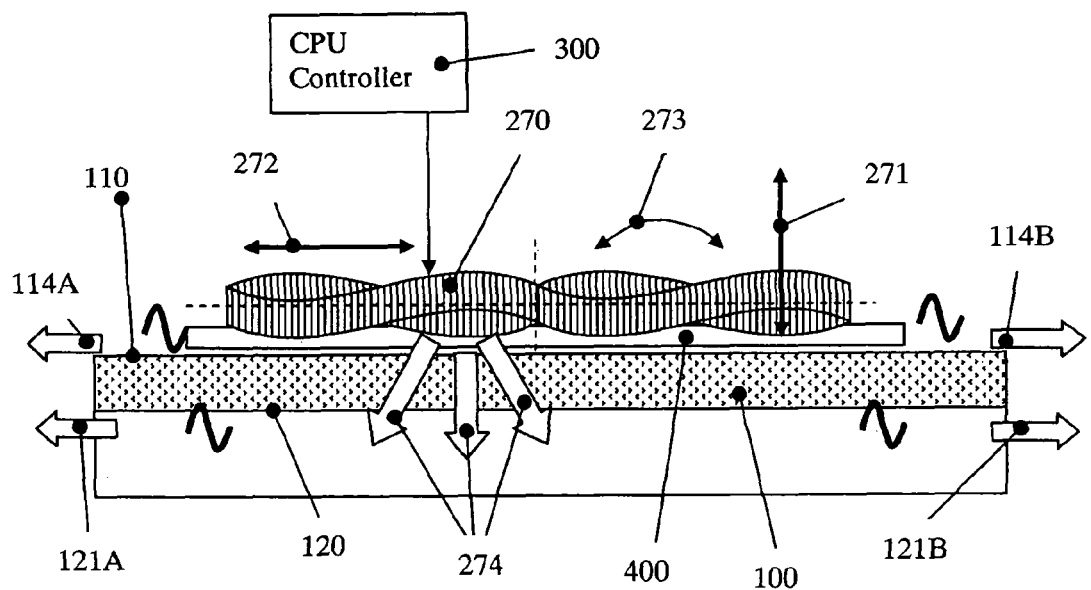
FIG. 7 is a schematic illustration of the method when the resonator is attached on an external or internal or end surface of a medical device for development of controlled SAW processes on these surfaces (thin piezo resonator is excited to vibrate simultaneously in three vibration modes: bending, longitudinal and thickness)

FIG. 7 shows the method wherein resonator 270 is attached on external or internal or end surfaces of the medical device for development of controlled SAW processes on these surfaces. For such a target, thin piezo resonator 270 is excited to vibrate simultaneously in three vibration modes: thickness 271, longitudinal 272 and bending 273. The minimal frequency for bending mode 273 should be chosen so as to ensure the distance between two friction points (the two points between max amplitudes) to be not less than SAW wave length on the surface; see FIG. 8. The frequency of electrical signals applied to the thin piezo plate is chosen with respect to thickness mode frequency 271. This electrical signal in CPU 300 is modulated simultaneously with two more frequencies, respectively for longitudinal 272 and bending 273 modes. Thin piezo plate 270 through coupling system 400 is tightly attached to external surface 110 of the medical device 100. Thereby, SAW vibrations on external 110 and internal 120 surfaces are excited simultaneously by the three modes of mechanical vibration. The running waves on external surface have positive 114A and negative 114B directions.

Mechanical energy transmission from the resonator to the internal surface 120 occurs in the following manner. The mechanical energy is transmitted in the direction 274 by plane longitudinal waves through coupling system 400 and through material distance between external 110 and internal 120 surfaces and has the character of bending mode frequency. As a result, the level of mechanical energy is time modulated by longitudinal 272 and bending 273 frequency modes and SAW having 121A and 121B directions on the internal surface.

Different frequency ranges can be achieved by combining vibration type (thickness, longitudinal, bending) of different harmonics ($1^{st}$, $2^{nd}$, $3^{rd}$, $4^{th}$). The effect can be achieved by either attaching the resonators internally or externally to the medical device surface. It should be understood that the attachment of elements externally results in a stronger vibrating effect on the external surface.

Figure 8:
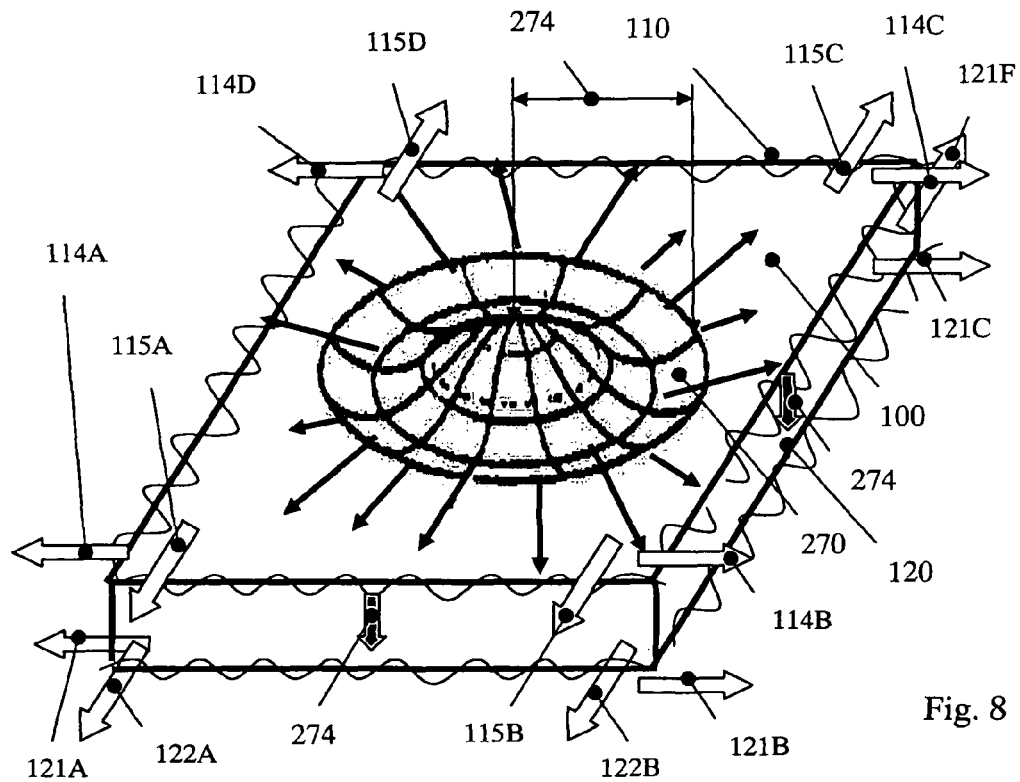
FIG. 8 illustrates a circular thin piezo membrane vibrating in bending (natural) mode.
Figure 9A:
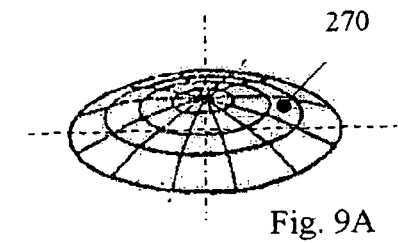
FIGS. 9A, 10A, 11A and 12A are the graphic illustrations of the normal vibration modes of circular membrane shapes for different n and m.

FIG. 8 illustrates a circular thin piezo membrane 270 vibrating in bending (natural) mode. The membrane 270 parameters of natural vibration mode are: n=0 and m=1. This membrane may symmetrically mechanically vibrate with respect to its rotation axis. The propagated SAW on the external surface 110 should have 114A, 114B, 114C, 114D and 115A, 115B, 115C 115D directions. Analogously, SAW may be propagated on internal surface 120 in the directions 121A, 122A, 121B, 122B (the other directions not shown). FIG. 9 diagrams the possibility of changing the direction and level of SAW propagation by manipulating the parameters of the vibration modes of thin circular piezo membrane 270. FIGS. 9A, 10A, 11A and 12A present graphic illustrations of the normal modes of circular membrane shapes for different n and m means.

Figure 9B:
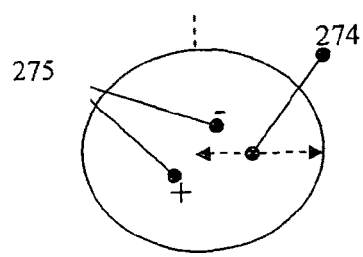
FIGS. 9B, 10B, 11B and 12B are schematic illustrations on the same mode.
Figure 10A:
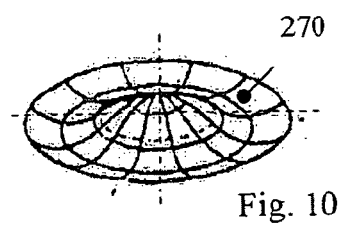
Figure 10B:
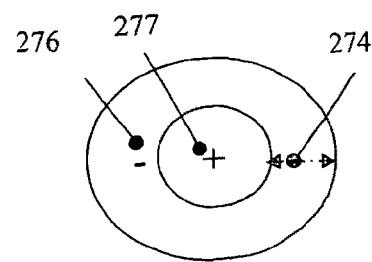
Figure 11A:
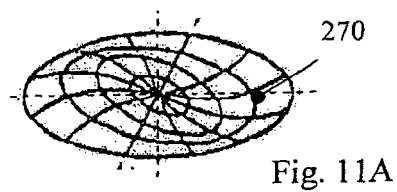
Figure 12A:
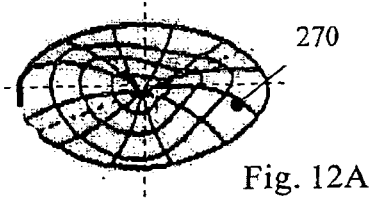
Figure 11B:
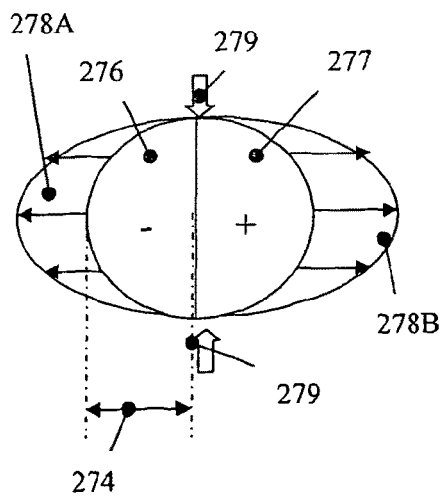
Figure 12B:
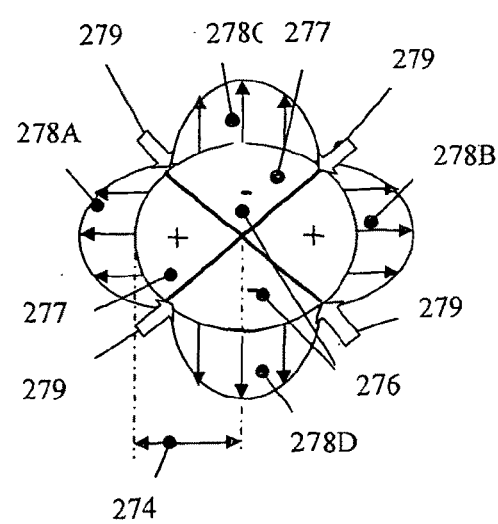

FIGS. 9B, 10B, 11B and 12B are schematic illustrations of the same mode. When circular membrane shape thin piezo element 270 has n=0 and m=1, as shown in FIGS. 9A and 9B, it has one only peak displacement mean. The distance between the peak and the edge of the membrane should be equal to at least ¼ of SAW wave length. If n=0 and m=2, as shown in FIGS. 10A and 10B, then piezo element 270 has two maximum amplitude peaks—negative 276 and positive 277. In this case, minimum SAW ¼ wave length corresponds to distance 274, which is smaller than in FIGS. 9A and 9B.

FIGS. 9 and 10 show that in the case where piezo element 270 has a circular membrane shape, it is possible to arrange a homogeneous SAW propagation process around the element. Furthermore, if vibrations with parameters of n=1 and m=1 are excited (see FIGS. 11A and 11B) in thin piezo element 270, the result will be two maximum amplitudes 276 and 277. The propagation directions of SAW 278A and 278B are relatively symmetrical. SAW process is not excited at the points 279, because vibration amplitudes in these points are equal to 0. A similar process is excited in the membrane 270 when n=2 and m=1, with four max peak displacements—two negative 276 and two positive 277. Propagation of the SAW process has four directions 278A, 278B, 278C and 278D and has zones 279, where the SAW process is not excited. In conclusion, by changing n and m vibration modes of the membrane, different SAW processes may be excited with the same thin piezo element. Distances 274 should be proportional to SAW wave length. Analogous SAW processes may be excited when the piezo element has a rectangular membrane shape. FIGS. 13A, 14A, 15A and 16A are graphical illustrations of the normal modes of a rectangular plate 280. FIGS. 13B, 14B, 15B and 16B are schematic illustrations of the same modes for different n and m. Membrane 280 has one max amplitude displacement 281, if n=1 and m=1, as shown in FIGS. 13A and 13B. In the case when n=2 and m=1, SAW process has two max displacement amplitudes 282A and 282B and two zones 283, where vibrations are not excited, as shown in FIGS. 14A and 14B. In the case where n=2 and m=2, the SAW process has four max displacement amplitudes—two positive 282A and two negative 282B, as well as four zones 283, where vibrations are not excited. See FIGS. 15A and 15B. In the case where n=2 and m=4 (as shown in FIGS. 16A and 16B0, the SAW process has eight max displacement amplitudes—four positive 282A and four negative 282B. The process has eight zones 283 where vibrations are not excited.

Achievement of SAW excitement on the medical device requires that the vibration modes, harmonics, lengths of periods, generated in the piezo element correspond to SAW length of the medical device. Rectangular piezo elements may excite different SAW propagations in the directions of the elements length and width (this may be of importance where different materials are used in the structure of the medical device and different SAW should be excited).

FIG. 14B illustrates membrane 280 and the excited mechanical vibration mode of thin piezo plate in the length direction with one appropriate period. FIG. 15B illustrates the case where the excited mechanical vibration mode of the thin piezo plate has one period in the length direction and in the width direction. FIG. 16B shows the case where the mechanical vibration mode of the thin piezo plate when excited, has one period in the length direction and two periods in the width direction. The stability of excited SAW process of the medical device corresponds to the number of vibration mode periods generated in the piezo plate (more periods means a more stable SAW process). Circular and rectangular shapes are not the only shapes suitable for biofilm prevention by means of exciting the SAW resonators. The same vibration modes may be excited with resonators having different geometry.

Figure 17:
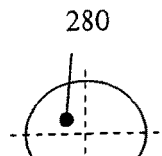
FIGS. 17-24 are schematic illustrations of several proposed circular shape resonators for biofilm prevention on a medical device surface.
Figure 18:
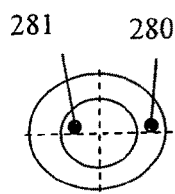
Figure 19:
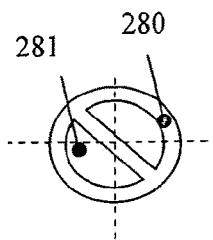
Figure 20:
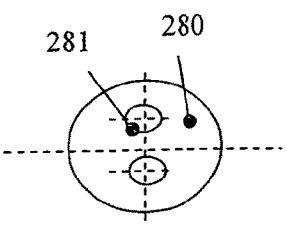

FIGS. 17-24 illustrate several other proposed circular shape resonators for biofilm prevention on a medical device surface. FIG. 17 shows a disk shape thin piezo element 280. FIG. 18 shows a ring shape thin piezo element 280 having an aperture 281. FIG. 19 shows a special shape thin piezo element 280 with holding apertures 281. FIG. 20 shows a disk shape thin piezo element 280 having two or more holding apertures 281. The edge areas surrounding the holding apertures serve as additional vibration excitement sources.

Figure 21:
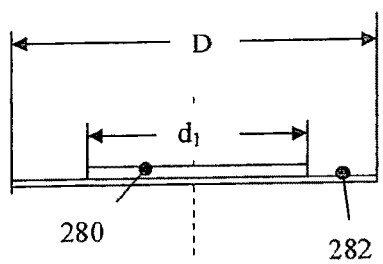
Figure 22:
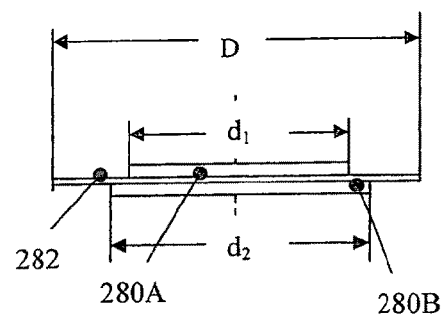
Figure 23:
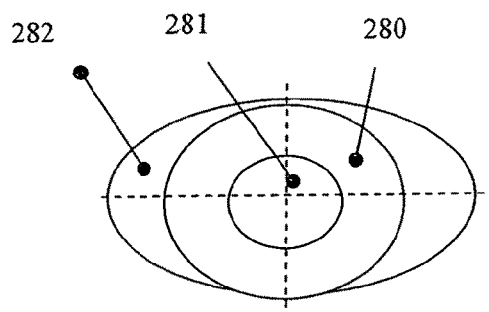

FIGS. 21-24 illustrate the merits of a buzzer type element for exciting SAW on the surface of a medical device. The buzzer geometry enables use of a very thin piezo material layer mechanically attached to a thin disk shape layer formed of metal or electrically conductive plastic. Such multi layer structured thin piezo elements with different D, $d_1$ and $d_2$ enable creation of natural vibration modes with high n and m harmonic values. FIG. 21 shows a thin disk shape piezo element 280 attached to disk shape support plate 287. The support plate 282 may be produced of metal, plastic or composite having conductivity properties. FIG. 22 shows such an element consisting of piezo disks 280A and 280B with respective diameters $d_1$, and $d_2$ attached to both sides of the plate 282 having diameter D. FIG. 23 shows an embodiment wherein piezo element 280 together with plate 282 has an aperture 281. One or several piezo elements 280, which are electrically isolated by elements 283, may be attached on one side of the plate 282. By means of applying different frequency signals to these piezo elements, vibration forms can be created of different natural modes. Experimental results have proven that in order to increase stability of the standing wave while using second and higher harmonics of thin bimorph piezo element, the piezo material layer should be cleaned off at the central part of the plate. The optimal (from the point of view of energy efficacy) nanovibration coating process on the surface of the medical device may be achieved, when relation between piezo material layer and metal layer in the bimorph element is in the range of about 0.95 to about 1.35.

Thin piezo elements exhibit the advantage of producing a more uniform nanovibration coating on the surface of the medical device. This feature is desired when the same SAW resonator is being attached to several medical device types that differ one from another in materials, geometrical parameters and properties of biofilm attachment effect.

Figure 25:
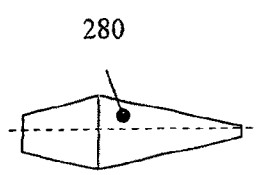
FIGS. 25-34 are schematic illustrations of several proposed thin piezo element constructions when geometry of medical device requires use of piezo plates.
Figure 26:
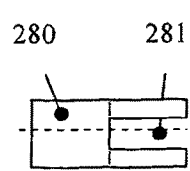
Figure 27:
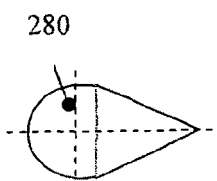
Figure 28:
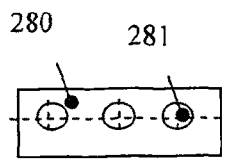

FIGS. 25-34 illustrate several proposed thin piezo element constructions, when geometry of the medical device requires use of thin piezo plates. The same construction piezo elements can be used even when different SAW processes are required to the medical device surface. Geometry and material of certain medical devices may require excitation of different SAW processes in order to achieve homogeneous biofilm prevention. FIG. 25 shows a thin plate type piezo element, the edges of which excite different SAW processes. FIG. 26 shows piezo plate 280 having a rectangular aperture 281. Combined form piezo plates 280 are shown in FIGS. 27-28.

Figure 29:
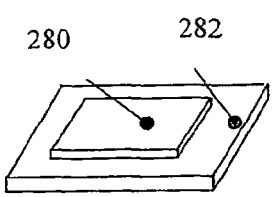
Figure 30:
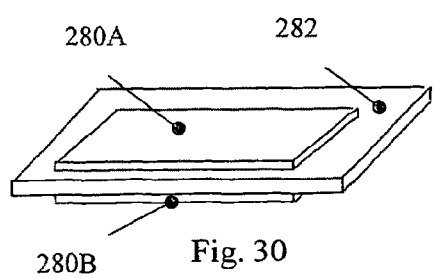
Figure 31:
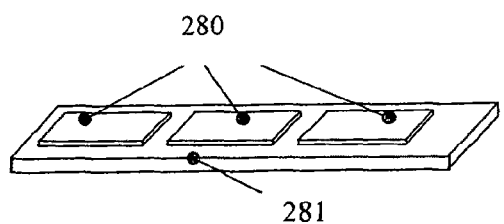
Figure 32:
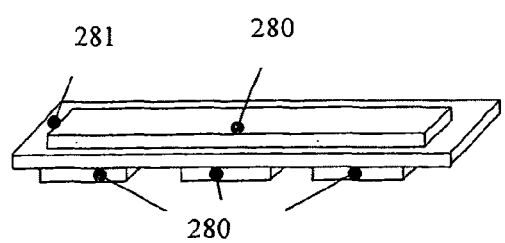
Figure 33:
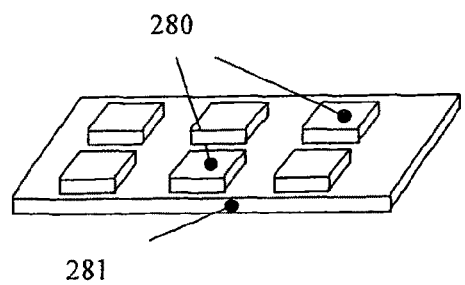
Figure 34:
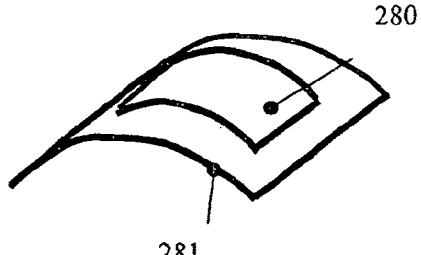

FIGS. 29-33 illustrate the application of bimorph type piezo elements. FIG. 29 shows a simple bimorph plate consisting of one thin piezo plate 280 attached to a metallic support 282. FIG. 30 shows two piezo elements 280A and 280B attached to one support plate 282. FIG. 31 shows more than one piezo elements 280 mechanically attached to one support plate. FIGS. 32 and 33 show other proposed variations for attachment of piezo elements 280 to metallic support plate 282. FIG. 34 illustrates the application of thin shell type bimorph piezo element. The layout of piezo elements 280 respectively the plate 282 may include all possible variations as was described hereinabove.

Figure 24:
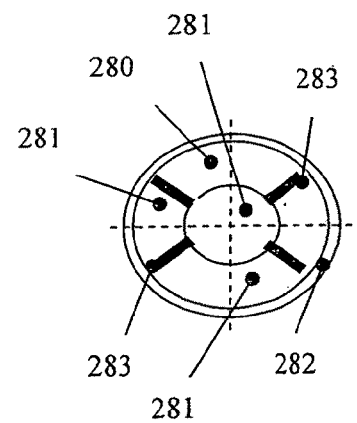
Figure 35:
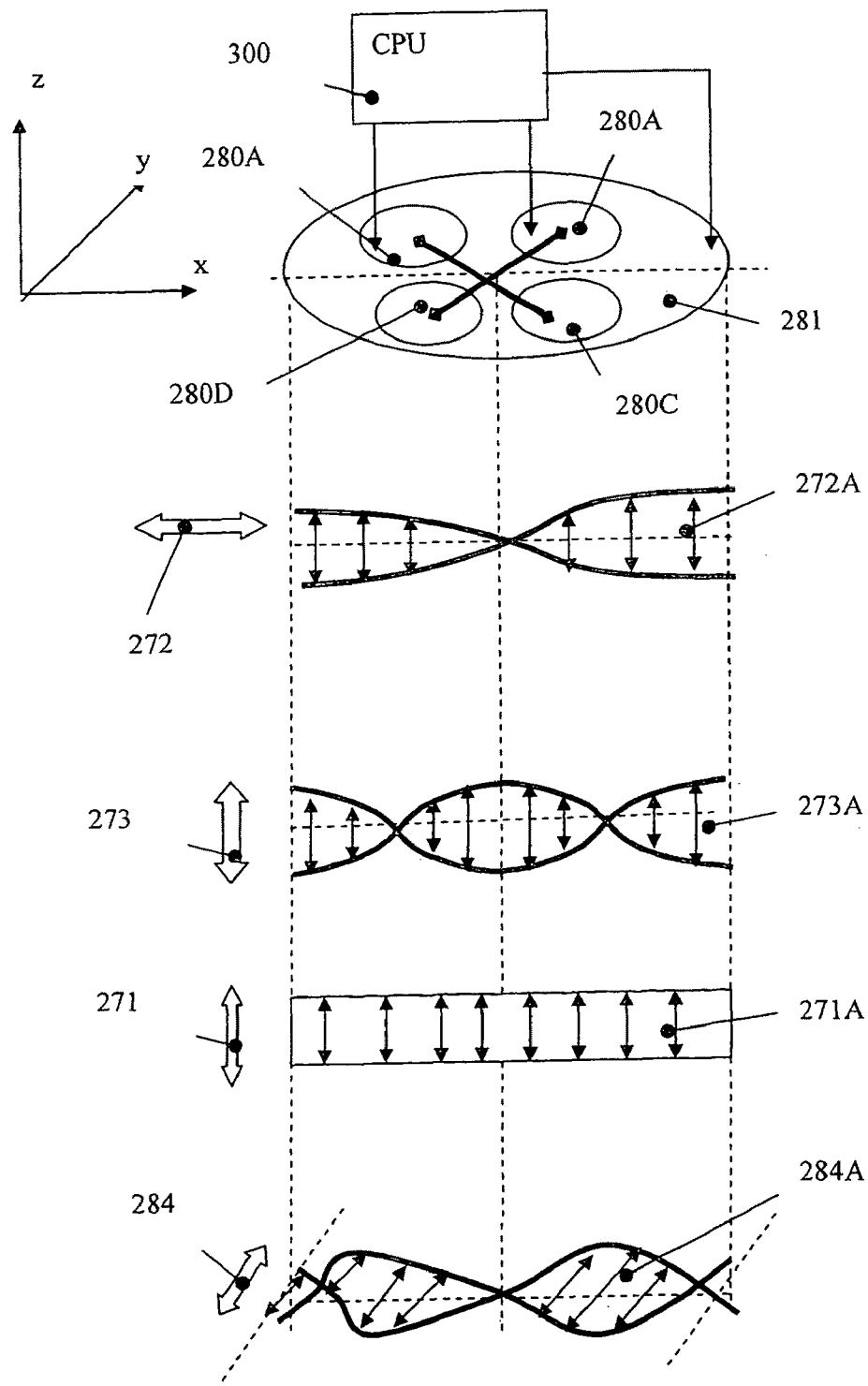
FIG. 35 is a schematic illustration of a proposed application with discrete piezo elements on a single resonator.

FIG. 35 explains the proposed application with discrete piezo elements on a single resonator. The method allows excitation of an additional vibration mode, more precisely a bending mode along an axis of symmetry in a longitudinal direction of the piezo plate seen in FIG. 35. The SAW resonator simultaneously can excite four types of vibration modes, these being the x, y, z axes. Graphical illustration 272A of longitudinal vibration mode 272 in y-z plane, thickness vibration mode 271 shown in graphic 271A, two bending mode vibrations 273 in z-x plane shown in graphic 273A, and another bending mode 284 in plane y-x shown in graphic 284A. This may be achieved through attachment of four piezo element parts 280A, 280B, 280C and 280D onto single plate 281. These parts are electrically connected in such a manner: 280A with 280C and 280B with 280C. A special embodiment may be a single piezo plate or a single piezo disk, as shown in FIG. 24, where electrodes connect to separate islands on a piezo element. When CPU 300 submits an electrical signal to parts 280A and 280C, the thin piezo element resonator begins to vibrate with a frequency corresponding to plate bending mode 284 resonance in plane x-y. By submitting the same electrical signal to parts 280B and 280D, the thin piezo element resonator begins to vibrate in opposite manner by phase bending vibration mode 284 resonance. If it is desirable to strengthen bending vibration mode 273, polarization of parts 280A and 280B should be opposite in respect to polarization of parts 280C and 280D. As a result of applying an electrical signal modulated by resonance frequency of the above mentioned mechanical vibrations from CPU 300 to resonator, SAW may be excited on the medical device featuring different forms and levels. These may be controlled in a desired direction and may be transferred to the inner surface as well. While creating second higher harmonics of standing wave in thin piezo element, the effectiveness of nanovibration coating process is increased about 30% in comparison with standing wave of first harmonics.

Multi vibration resonators may be attached to the actual medical device or formed as an integral unit with the device. There may be several attachment types for SAW excitement: hard gluing, mechanical attachment, spring type attachment. The proposed hard type attachments (gluing, mechanical) assure a constant position of the resonator on the medical device. The spring type attachment allows movement of the resonator in respect to the medical device surface.

FIGS. 36-44 illustrate the attachments of the above described resonators 280 to medical device 100 or different parts thereof. The proposed examples may be applicable while integrating piezo resonators into new designed medical devices. One or more SAW process resonators may be attached to a single medical device.

FIG. 42 explains the proposed application of a single piezo resonator 280 for SAW generation on different parts of medical device 101 and 102. FIGS. 36-38 explain the proposed attachment variations of the same piezo plate 280 to medical device 100. The orientation of the plate in respect to the medical device should be chosen in consideration to the desired SAW process and medical device design features (geometry). FIG. 39 shows the attachment of a shell type piezo plate 280. FIG. 40 shows the proposed circular segment shape thin piezo plate 280. Applications using two or more piezo plates 280 are schematically shown in FIGS. 41 and 43. FIG. 44 illustrates the proposed invention where the medical device holding element 280 consists of shell type piezo elements 280.

A high concentration of viscous, sticky particulate matter may lead to accretion. The devices can become coated with layers of this particulate matter-accretion. In such circumstances, the establishment of accretion does not inhibit the SAW process or operation of the process effectively upon the surface of the accreting matter.

Figure 45A:
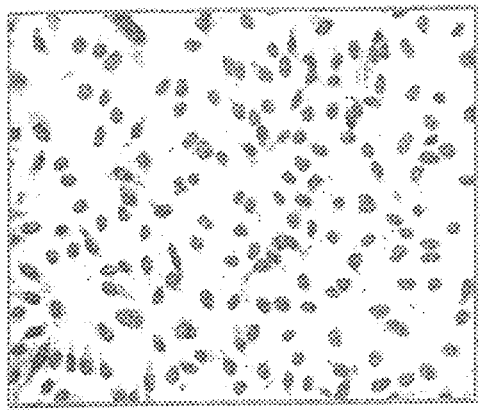
FIGS. 45 (A, B, C) illustrate electronic microscopy results of in-vitro safety experiments of excited SAW with respect to bioeffects (effect on attached monolayer cells in tissue cultures)
Figure 45B:
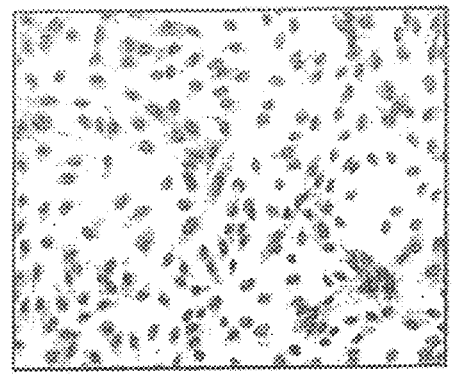
Figure 45C:
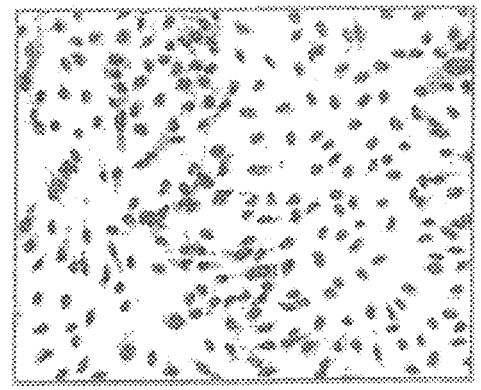

FIGS. 45 (A, B, C) illustrate results of our in-vitro experiments to prove the safety of excited SAW with respect to bioeffects (on attached monolayer cells in tissue cultures). In the following experiments, we simulated the different energy levels emanating from the medical device on the inner surface of a tissue flask.

These experiments were aimed to examine effects of the nanowave treatment on human cells in monolayer tissue culture. The U87MG human Glioblastoma cell line and ARPE19 human retinal pigment epithelial cell line (normal, non carcinogenic) were examined. The cells were plated in 25 cm$^2$ tissue culture flasks (Corning) to which resonators were glued to the external surface of the flasks in order not to compromise their sterility. The devices were activated in a 37° C., 5% $CO_2$ tissue culture incubator for a period of 48 hours. The cultures were then washed with PBS, fixed with methanol, stained with May-Grunwald Giemsa and examined microscopically. Resonators were glued to the external bottom surface of 25 cm$^2$ tissue cultures flasks (from Costar). One set of elements generated a frequency of 220 KHz with acoustic pressure amplitude of 0.22 KPa. Another set of flasks were glued with elements generating frequencies of 285 KHz, 1.2 KPa.

The results are shown in FIG. 45. As can be seen, cells in the active (45B, 45C) group maintained normal morphology, there was no evidence or occurrence of programmed cell death (apoptosis) as apoptotic bodies (containing fragmented nuclei) are not seen. There is also no evidence for cell monolayer destruction, for dead cell debris or for induction of cell death by necrosis. We could not detect any adverse effects of the treatment on either of the cell cultures.

Applications described here below illustrate the variety of cases where the problem of preventing biofilm formation is important. Indwelling medical devices such as peripheral, especially central venous catheters, are used with increasing frequency in the intensive care and in general medical wards to administer intravenous fluids and blood products, drugs, parenteral nutrition. Catheter colonization is one of the risk factors associated with intravenous catheters. Therefore, of great importance is the ability to form surface acoustic waves (virtual nanovibration coating process) all over surfaces of a medical device by means of communicating small mechanical vibration energy to the medical device, effecting in inhibiting of bacteria attachment and the entry of microorganisms from external and internal sources. In addition, the SAW process reduces friction and mechanical stress during introduction and withdrawal of the medical device.

The controlled SAW process enables pushing or pulling materials, including fluids and particulates suspended in them, along the medical device surfaces. In some cases, it may be useful to utilize different vibration energies to create different conditions and encourage growth of selected bacteria in preference to others. This means to select bacteria that differ in their ability to attach and form communities.

Figure 46:
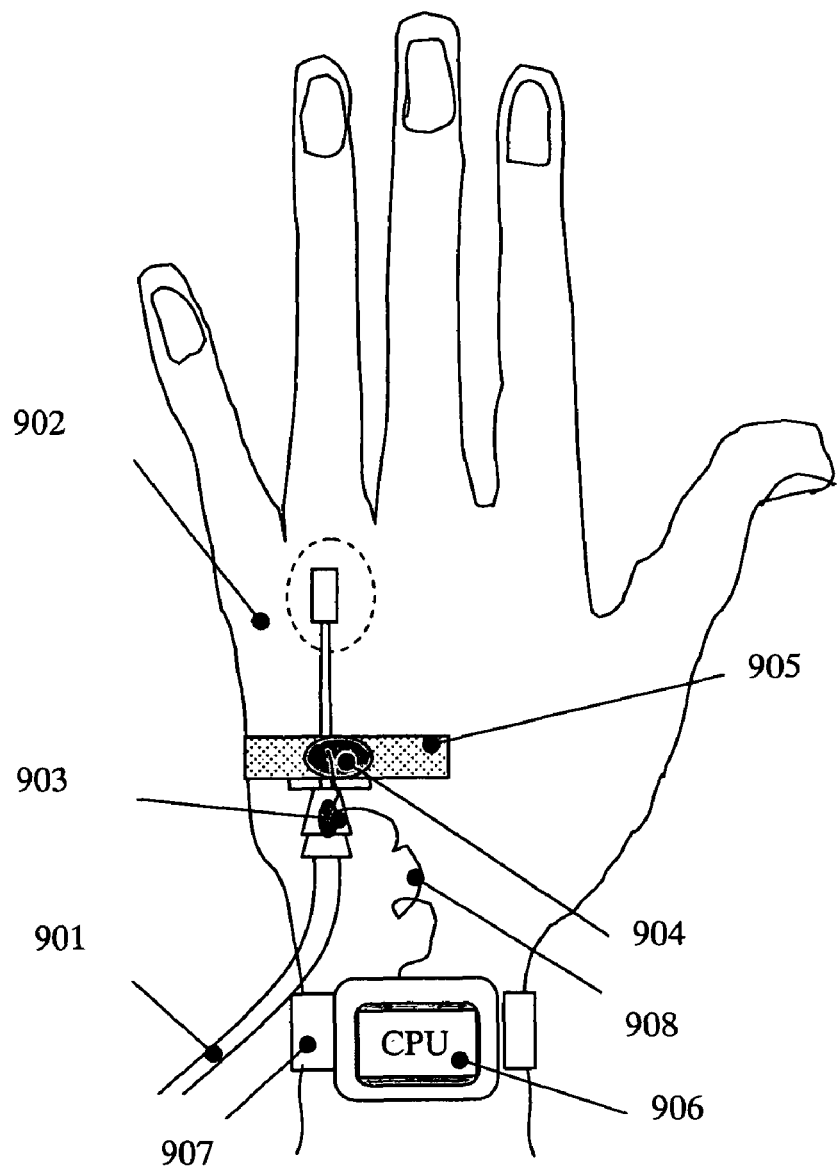
FIG. 46 illustrates proposed application of the technology with standard peripheral intravenous catheter system.

FIG. 46 illustrates one more proposed application of technology with standard peripheral intravenous catheter system consisting of catheter 901 with tube. This catheter is the typical "hospital IV" line applied to patient hand 902 or forearm (not shown). At least one thin piezo resonator 903 is attached to a hub of the catheter. Piezo resonator 903 may include features of detection and sensing on SAW processes. The excitement of piezo resonator 903 proceeds through CPU 906. At the contact zone between tissue and medical device, the SAW process focuses transversal mechanical energy which effects the surrounding tissues and prevents the establishment of biofilms. The effect is extended to a surrounding distance of several millimeters. Biofilm is prevented, not only on the device, but also on the adjacent tissues. This effect corresponds to a vibration wave length up to 5 cm. Furthermore, frequent thrombus and attachment of matter on the tip is prevented as a result of reduced friction of the liquid, flowing through the device regardless of the direction.

Figure 47:
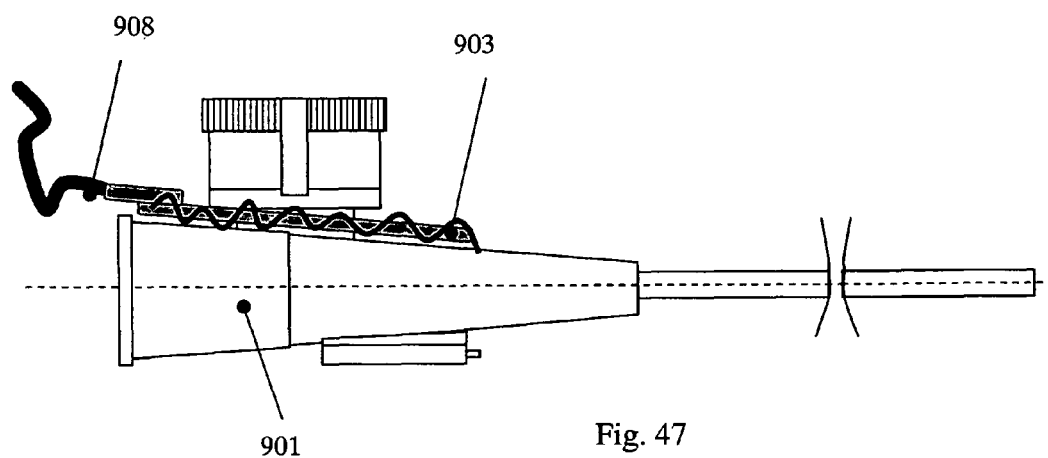
FIGS. 47 and 48 are graphical illustrations of embodiments wherein a thin piezo element has the shape of a thin ring segment, which is mechanically attachable or integrated into a catheter connector.
Figure 48:
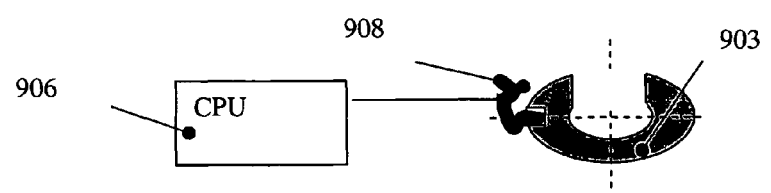

FIG. 46 illustrates several methods to connect the piezo resonator with peripheral intravenous catheter system when the latter is attached to patient's hand 902. The first type is where the thin piezo resonator has the shape of a thin ring segment 903 (as it is shown in FIGS. 47 and 48) mechanically attachable or integrated into the catheter connector. Another application is shown in FIGS. 46 and 49 where piezo resonator 904 (one or more) is integrated into adhesive tape 905.

Figure 49:
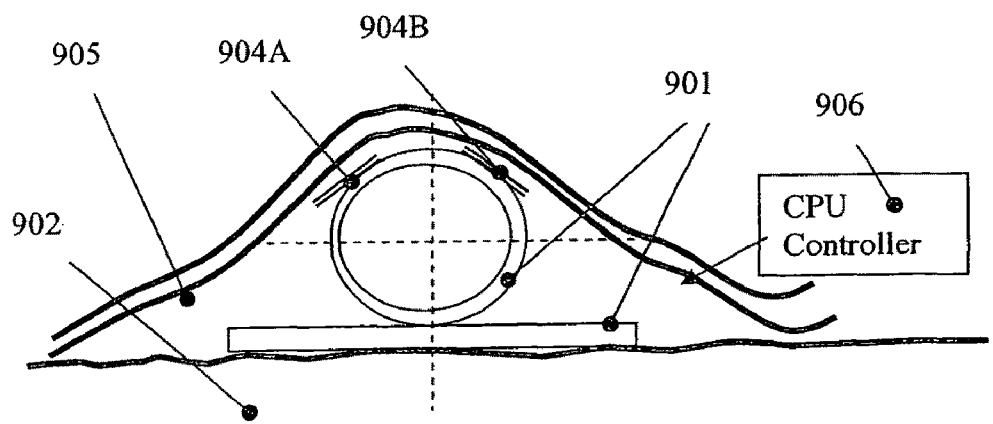
FIG. 49 illustrates another application wherein piezo resonator (one or more) is integrated into an adhesive tape.

FIG. 49 shows adhesive tape 905 with two thin piezo resonators 904A and 904B, which may be attached to catheter system 901 for target to generate nano vibration coating process. Piezo resonators 904A and 904B include sensor and actuator features for generating SAW and sensing this process. Piezo resonators 903 and 904 are excited by signals from CPU 906 through a variety of controls. See FIG. 46. CPU 906 may have an attachment to the patient hand 902 by means of belt 907, or by other means, for example by gluing tape. CPU 906 is connected with piezo resonators 903 and 904 (together or separately) by means of wire 908.

FIG. 49 illustrates another application of the proposed invention, when CPU 906 is connected to piezo resonators 904A and 904B, the resonators and their electrical wires being attached to the medical device with adhesive tape 905. CPU 906 is capable of generating vibrations and receiving electrical signals from these elements. The work of CPU 906 was described above and scheme shown in FIG. 2. Furthermore, resonator 903 or 904 for generating a nano vibration coating process may be placed on any part of indwelling intravascular catheter.

Figure 50:
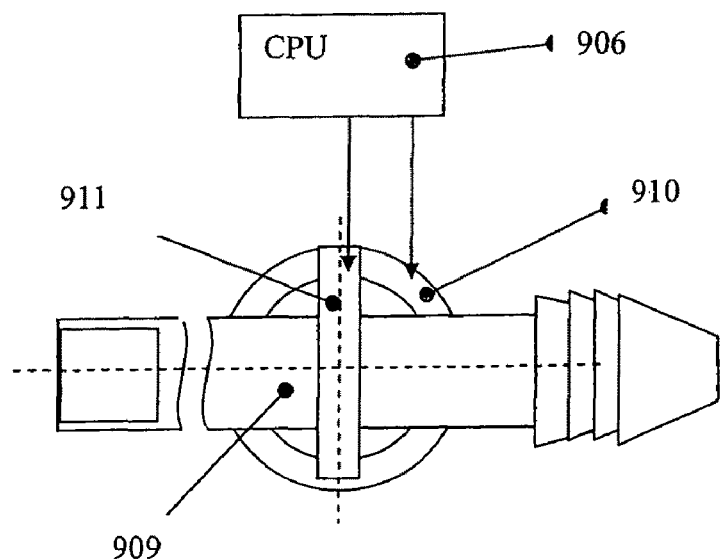
FIG. 50 illustrates special shape thin piezo disk-ring element attached to intravenous catheter connector.

FIG. 50 illustrates a special shape of a thin piezo disk-ring plate 910 attached to connector 909. An inner plate 911 of the disk-ring plate 910 serves as attachment to the connector. Plates 910 and 911 may not only generate SAW (virtual nanovibration coating) but simultaneously act as sensors of SAW propagation on indwelling medical device parts.

Figure 51:
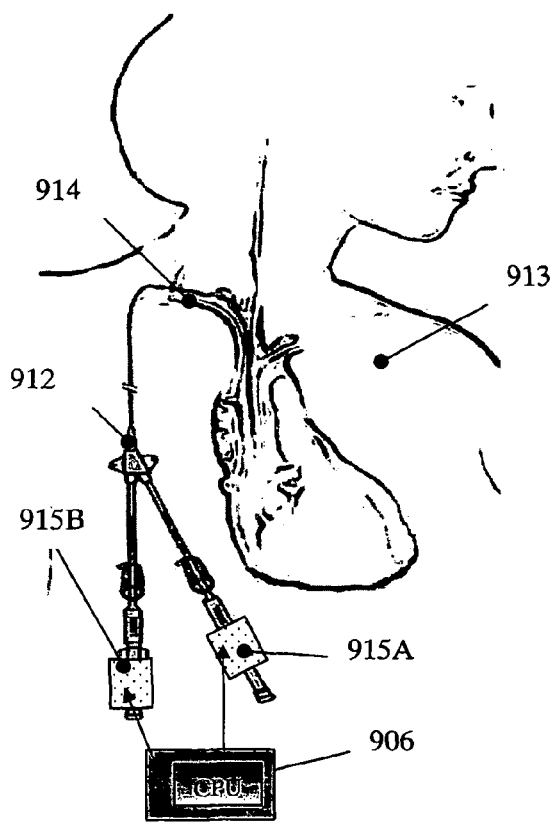
FIG. 51 illustrates two thin piezo elements attached to separate lumens of the central venous catheter.
Figure 52:
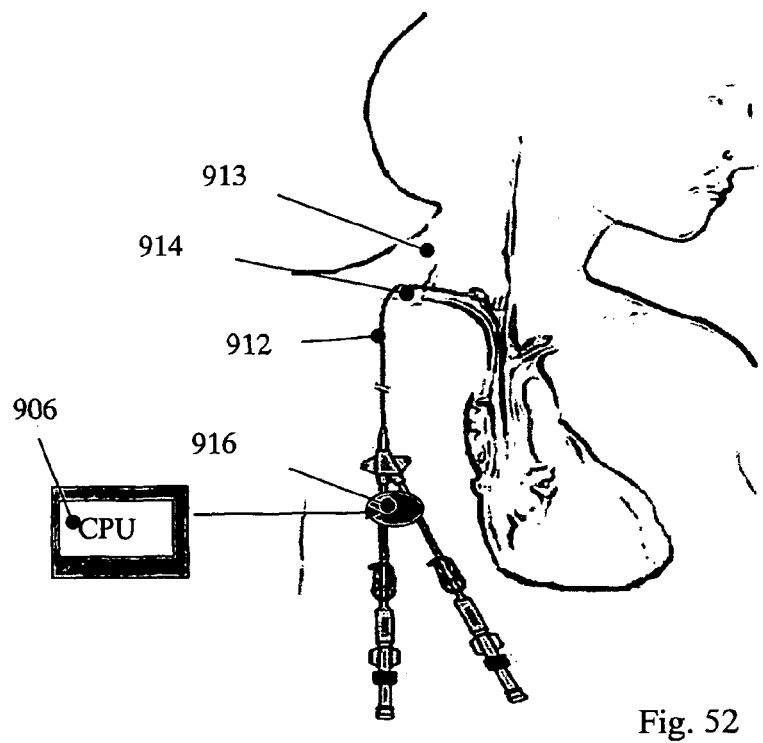
FIG. 52 illustrates another application of the proposed invention wherein an adhesive tape with thin piezo elements is used in a central venous catheter system.

FIGS. 51 and 52 illustrate a central venous catheter system 912 attached to patient body 913. Catheter system 912 is threaded through a vein in the neck (the external or internal jugular vein) or a vein in the upper chest under the collar bone (the subclavian vein) into a large central vein in the chest (the superior vena cava) 914. The two general types of catheter system 912, which are permanently placed under the skin 913: with no catheter coming out through the skin (an internal catheter), or those which come out through the skin (the external catheters). The synthetic substances used in the catheter system treatment of a patient interface with tissue at some stage and is related to complications. The proposed invention will optimize biocompatibility and decrease biomaterial related complications such as infection and encrustation within urinary tract, vascular lines, and those associated with implants. The inventive mechanism involves surface acoustic waves generating vibration of the structure material resulting in a decrease in the coefficient of friction of the biomaterial, which improves biocompatibility by reducing frictional irritation and cell adhesion at the biomaterial—tissue interface. The process of precipitation and formation of crystals (accelerated kinetically by the presence of rough surfaces, catheter holes and edges) will be reduced.

FIG. 51 illustrates two thin piezo plates 915A and 915B attached to separate lumens of the central catheter (an external part of the catheter) and electrically connected with CPU 906 for generating the nanovibration coating process. Plates 915A and 915B may work in the same or separate regimes while generating SAW propagation.

FIG. 52 illustrates another application of the proposed invention where adhesive tape with thin piezo plate 916 is used in a central venous catheter system. The thin piezo actuator plates 903, 905, 915A, 915B and 916 may be placed on any part of the intravenous catheter lines including 901 and 912, but not limited to fluid reservoirs, pumps or any ancillary equipment.

Figure 53:
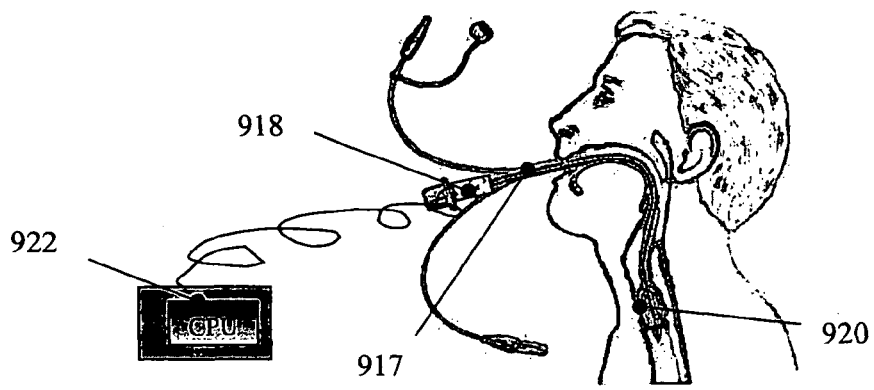
FIGS. 53-55 are graphical illustrations of other embodiments of the invention wherein different type SAW resonators are attached to endotracheal ventilation tube systems.
Figure 54:
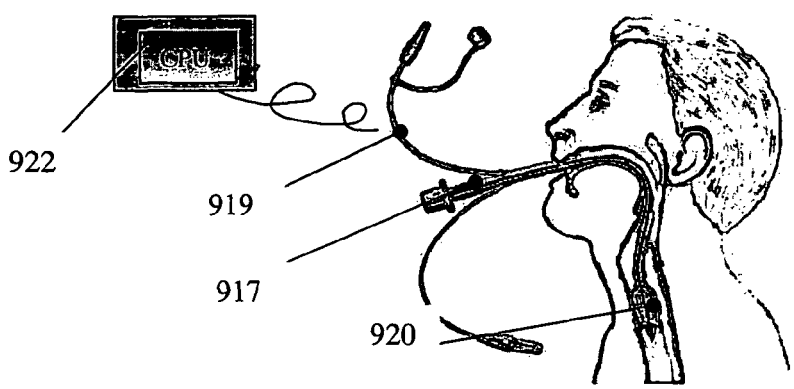
Figure 55:
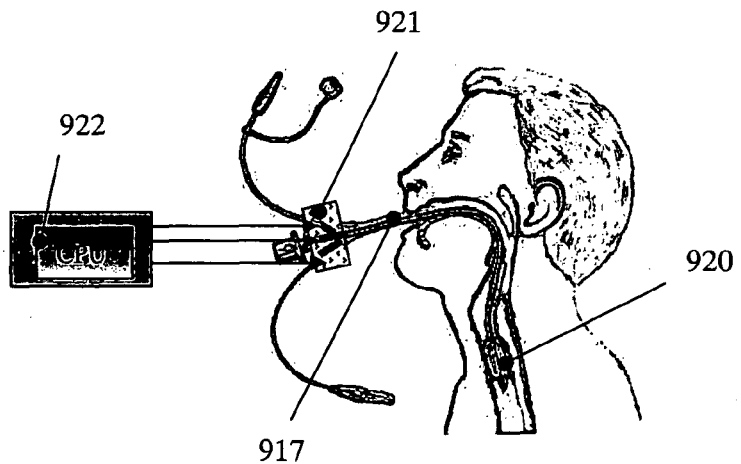

Biocompatibility problems are associated with another category of indwelling devices—endotracheal ventilation tubes. These are a major cause of death due to pneumonia resulting from biofilms. FIGS. 53-55 illustrate another embodiment of the invention wherein different types of SAW resonators are attached to the endotracheal ventilation tube system 917. FIG. 53 illustrates an embodiment with SAW resonator having a thin shell shape piezo element 918 attached or integrated into the central tube of catheter FIG. 54 illustrates an embodiment wherein the SAW resonator has a shape of a piezo disk 919 with attachment hole or integrated with the inflation channel of balloon 920. FIG. 55 illustrates another embodiment wherein SAW resonator has a multi piezo elements system 921 attached to separate lumens of the catheter system 917. CPU 922 enables the above mentioned SAW resonators 918, 919 and 921 to generate surface mechanical vibrations on the external surfaces of balloon 920. Scale of mechanical vibrations is in the range from 10 Hz to MHz. Duty cycle may vary from 1:1 to 1:1000. The scale of displacement amplitudes is nanometers. Acoustic power applied is less then 1 mW/cm$^2$. Endotracheal ventilation tube as the one illustrated in FIGS. 53-55 is equipment associated with high risk for becoming contaminated in standard practices of ventilation machines. Due to SAW process, the transverse vibration energy effects the contact fluids and the friction of the fluids is thereby reduced. Vibrations expel the fluid and promote the drying process at the point of contact with the skin which achieves resistance to bacteria entry.

CAUTIs (catheter associated urinary tract infection) are a cause for concern as they are major reservoir of resistant pathogens. The proposed invention of creating SAW on indwelling medical device surfaces and as a result prevention of these infections doubtless will be a critical step in the battle against antibiotic resistance.

Figure 56:
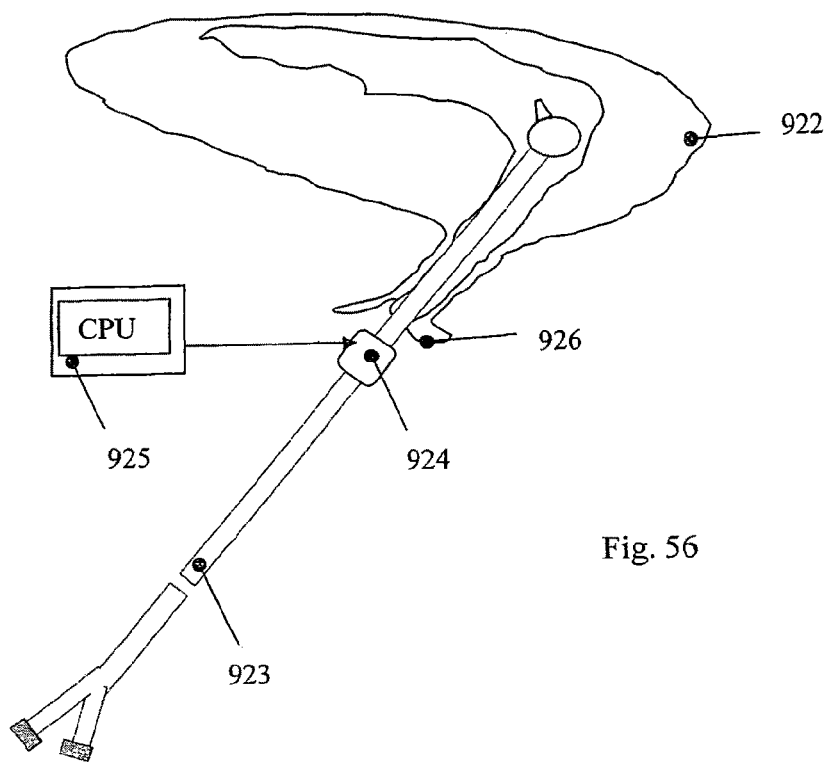
FIG. 56 illustrates the principle of another application of the proposed invention—the device "Uroshield" (type 010)
Figure 57:
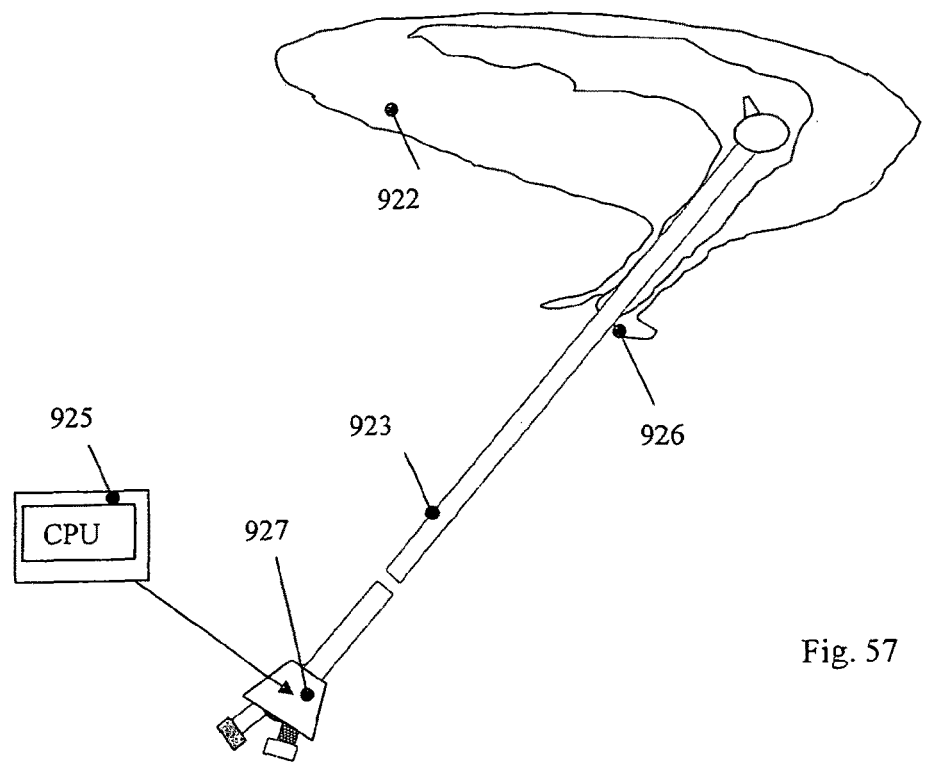
FIG. 57 is an illustration of another coupling solution for the Uroshield device wherein several piezo elements are attached at the cross points on the catheter.
Figure 58:
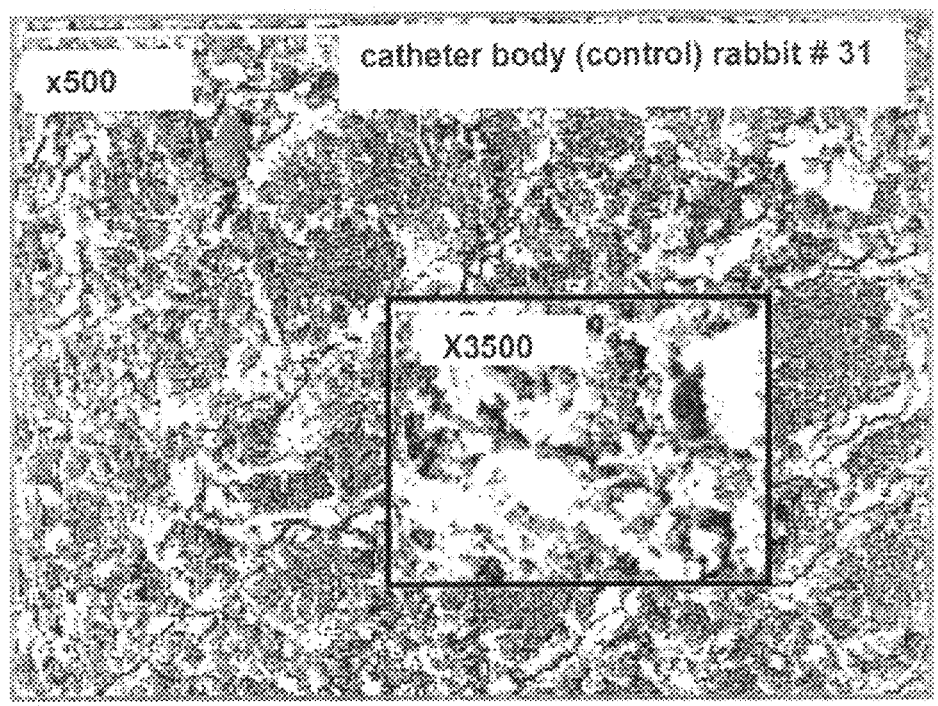
FIGS. 58-61 illustrate the results of in-vivo studies (SEM)
Figure 59:
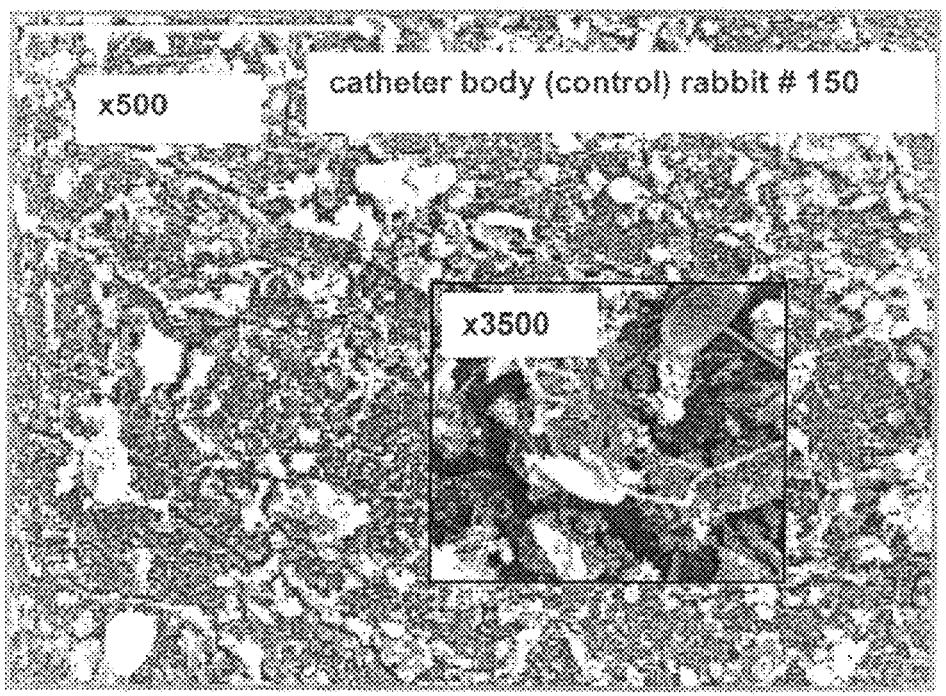
Figure 60:
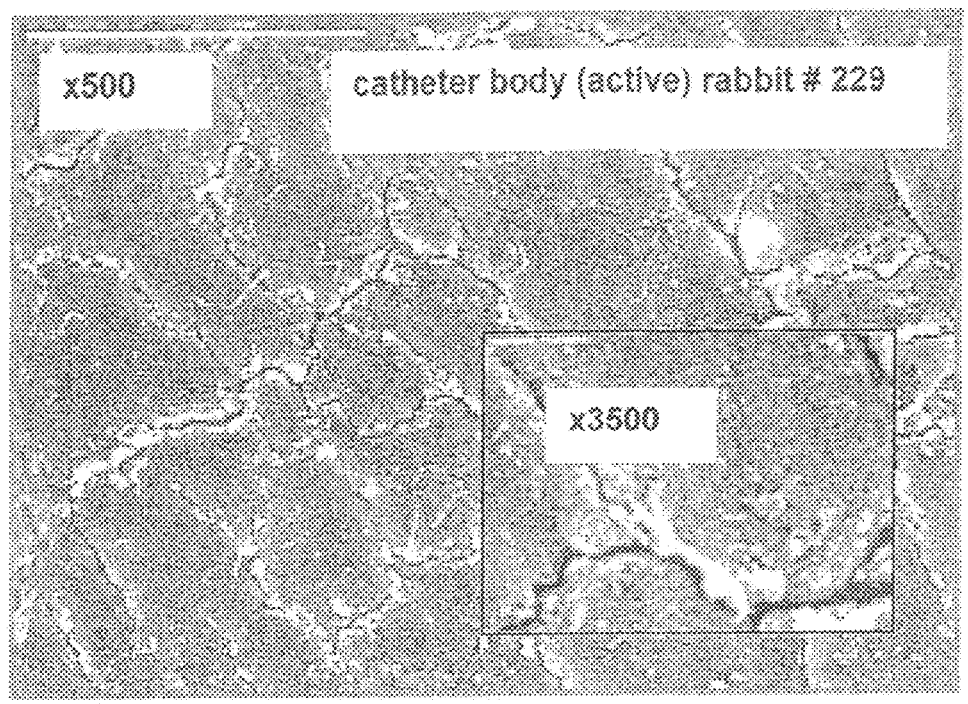
Figure 61:
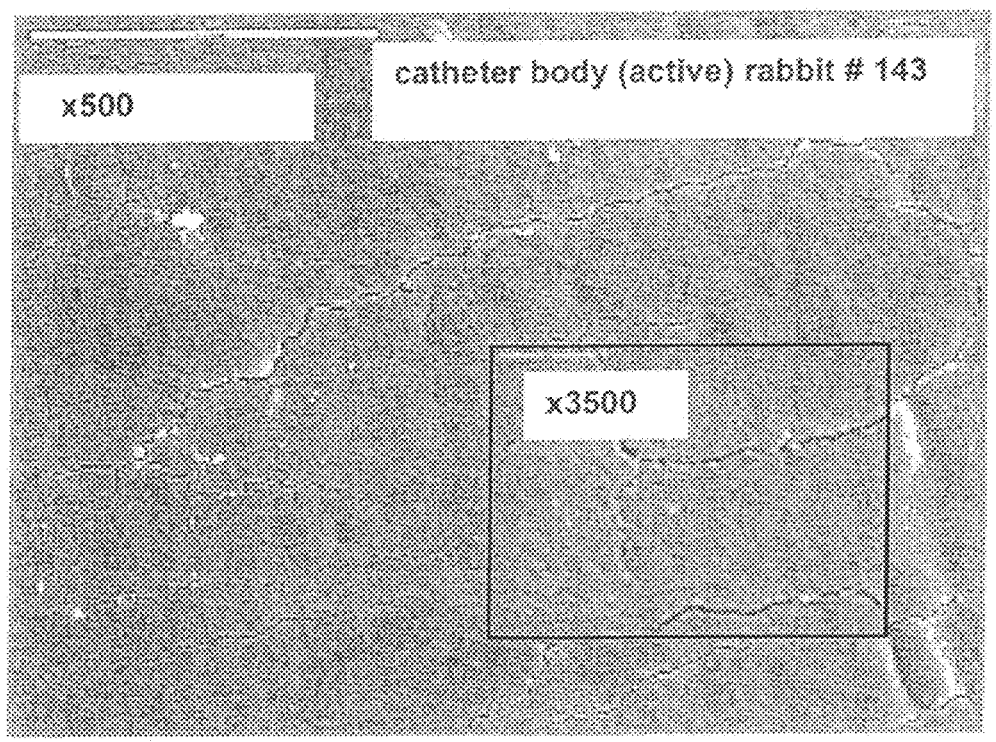

FIGS. 56 and 57 are schematic illustrations of optional SAW generation process applications for urinary tract system 922. FIG. 56 shows urinary catheter tube 923 with thin piezo element 924 attached and connected respectively to CPU 925. The catheter 923 with balloon is inserted into the urinary tract 922 and resulting from created mechanical nano scale vibrations, biofilm formation is prevented on all surfaces of the catheter 923. The generated SAW process features the extra aspect of a transverse character. This means the energy may be transferred to the tissues of the human body from external surfaces and transferred to biological matter in contact with the internal surface, from internal surface of the device.

FIG. 56 illustrates the principle of another application of the proposed invention—the device 924 "Uroshield" (type 010), which was designed and developed by Nanovibronix Inc. for biofilm prevention on urinary catheters. Another coupling solution for the same device is shown in FIG. 57. Several piezo elements 927 are attached to cross places on the catheter.

FIGS. 58-61 illustrate the results of in-vivo studies. The aim was to evaluate the safety and efficacy of the Uroshield (see FIG. 56) in delaying/preventing biofilm formation on urinary catheters in rabbits. Study endpoints included testing the efficacy of SAW in delaying/preventing bacteria and also in reducing or eliminating biofilm formation as determined by scanning electron microscopy (SEM). In addition, with safety as a goal, the effects were examined of the SAW on the urinary tract assessed by histopathology. Safety was examined by comparing the histopathological specimens of the urinary tract in both groups by means of:

1. The functioning of the UroShield assessed daily using a validation device measuring frequency, amplitude, connectors, current and acoustics in accord with a defined dossier of parameters.

2. At the end, the experiment animals were euthanized, autopsied and the catheter inside the urinary bladder and urethra removed together with the adjacent mucosa. The catheter was immersed in 4% buffered formaldehyde and taken for SEM (scanning electron microscopy) analyses. Urinary mucosal sections were collected in 4% buffered formaldehyde from the infundibulum of the urinary bladder, from the mid-bladder, trigonal area, proximal urethra and distal urethra for histological analyses. Catheter was divided into sections relative to acoustic power. The acoustic pressure amplitudes in emitting points on the catheter were divided: D—body; B—Balloon; Maximum acoustic pressure amplitude on different points of the urinary catheter: body—D, Pmax=0.14 (KPa); Maximum acoustic pressure amplitude on the urinary catheter balloon—B: Pmax=1.2 (KPa);

Results:

TABLE 1

Bacteriuria: Bacterial titers in the urine (CFU./ml)

| Rabbit No. | Bacterial titer | | | | | | | | |
|---|---|---|---|---|---|---|---|---|---|
| | Day 1 | Day 2 | Day 3 | Day 4 | Day 5 | Day 6 | Day 7 | Day 8 | Day 9 |
| 163-A | 0 | 0 | 0 | 0 | 0 | 0 | 0 | — | — |
| 229-A | 0 | 0 | 0 | 0 | 0 | 0 | 0 | 0 | 0 |
| 265-A | 0 | 0 | 0 | 0 | 0 | $10^4$ | $10^6$ | — | — |
| 143-A | 0 | 0 | 0 | 0 | 0 | $3 \times 10^3$ | $2 \times 10^4$ | — | — |
| 28-C | 0 | $1.4 \times 10^7$ | $5 \times 10^7$ | — | — | — | — | — | — |
| 31-C | 4 | $10^4$ | $5 \times 10^3$ | $10^4$ | 0 | 0 | $8 \times 10^8$ | $2.5 \times 10^8$ | |
| 150-C | 0 | 6 | $4 \times 10^6$ | $10^8$ | — | — | — | — | — |
| 144-C | 70 | $10^6$ | $5 \times 10^6$ | — | — | — | — | — | — |

A—Active device.
C—Control.
— refers to termination of experiment

TABLE 2

Summary of time to bacteriuria

| Rabbit No. | Indwelling time | Time to bacteriuria | Time in bacteriuria | Level of bacteriuria |
|---|---|---|---|---|
| 163-A | 7 days | Remained sterile | 0 | 0 |
| 229-A | 9 days | Remained sterile | 0 | 0 |
| 265-A | 7 days | 5 days | 2 days | $10^4$, $10^6$ |
| 143-A | 8 days | 5 days | 2 days | $3 \times 10^3$, $3 \times 10^4$ |
| 28-C | 4 days | 1 day | 3 days | $1.4 \times 10^7$, $5 \times 10^7$ |
| 31-C | 8 days | 1 day | 6 days | 2 last titers: $8 \times 10^8$, $2.5 \times 10^8$ |
| 150-C | 5 days | 2 days | 3 days | $4 \times 10^6$, $1 \times 10^8$ |
| 144-C | 5 days | 2 days | 3 days | $10^6$, $5 \times 10^6$ |

The findings show that:
Percent active animals remaining sterile throughout the experiment=50% (2 of 4)
Percent control animals remaining sterile throughout the experiment=0%
Average time to bacteriuria in active animals which developed infection=5 days
Average time to bacteriuria in control animals=1.5 days
All parts of the catheter were thoroughly examined: The SEM evaluations hereunder were performed by our research team.
Rabbit 229 (active, Body of catheter from rabbit #229)—Examination of all parts of the catheter (except the tip that was not available) did not reveal any characteristic biofilm formation or the presence of bacteria. The material on the catheter appeared to be cell debris, coagulated proteins, latex and silicone particles. Sperm cells were observed on the external surface of the body and the internal surface was extensively covered with crystals.
Rabbit 143 (active, Body of catheter from rabbit #143)—Some biofilms were found on the balloon only, while on other parts of the catheter no biofilms were found. Numerous erythrocytes were seen on the internal surface of the catheter.

Rabbit 31 (control Body of catheter from rabbit #31)—Heavy thick biofilms were observed on all parts of the catheter. Some of the biofilms were detached from the catheter. The latex and silicone were peeled and there was mucous tissue attached to the catheter.

Rabbit 150 (control, Body of catheter from rabbit #150)—The catheter was covered with biofilms and clusters of bacteria were scattered all around, particularly heavy on the balloon and the internal surface of the body. The silicone layer was peeling and sperm cells were scattered all over.

In summary: Sixty six percent of control catheters were covered by heavy biofilms and clusters of bacteria. Samples of catheters from rabbits 31 and 150 were heavily covered with biofilms, while the catheter from rabbit 28 exhibited only moderate biofilm structures scattered at different parts of the catheter. The surface of 75% of the active catheters were clean from biofilms and bacteria clusters. Samples of catheters from rabbits 163 and 229, which remained sterile (bacteriuria 0) for 7 and 9 days, respectively, were not covered with biofilms or bacterial clusters. Biofilms were observed on the surface of the catheter of rabbit 265 (despite the fact that the catheter was actively vibrated). However, rabbit 265 developed bacteriuria during the last 2 days of the study. The level of bacteriuria in the last day was $10^6$ CFU/ml, a level sufficiently high to enable formation of biofilms. These results suggest that formation of biofilms on the catheter surface correlates with the level of bacteriuria.

An independent blind examination of SEM figures of catheter samples was conducted by an electron microscopy expert.

The experimental results proved that in the case of biofilm developing both independently or dependently of the medical device, the introduction of nanovibration waves (a) reduced the existing biofilm, and (b) augmented and enhanced the effect of antibiotics on the biofilm (decrease the biofilm resistance to antibiotics). The ability to create directional nanovibration coating process with motion in accordance with natural drainage and flow of fluids produced by the body in that location (for external and tracheal fluid, urine, etc) results in the expulsion or slowing the penetration of bacteria to the body cavity. All these factors considerably delay infection.

The experimental results have proved that SAW resonators 924 and 927 as biofilm preventing devices may be placed on any preferred part of the medical device: connector, bag or any ancillary equipment (as it is shown in FIGS. 56 and 57).

Figure 62:
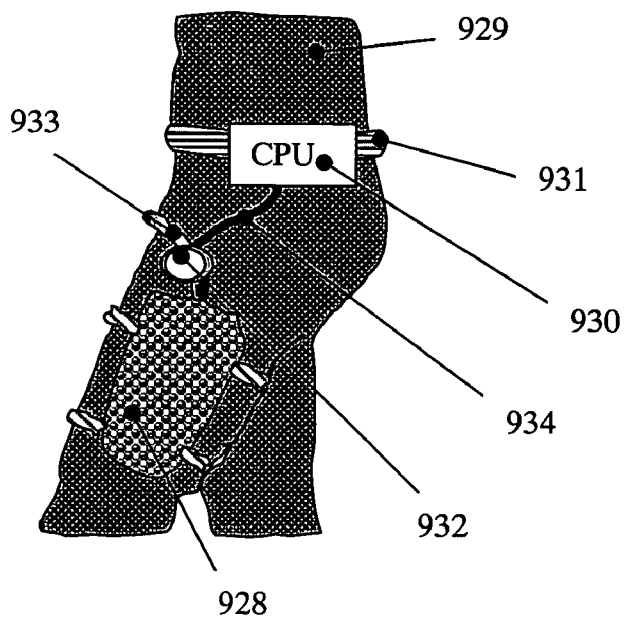
FIGS. 62 and 63 are schematic illustrations of possible variations when urinary bag can be attached to the leg of the patient.
Figure 63:
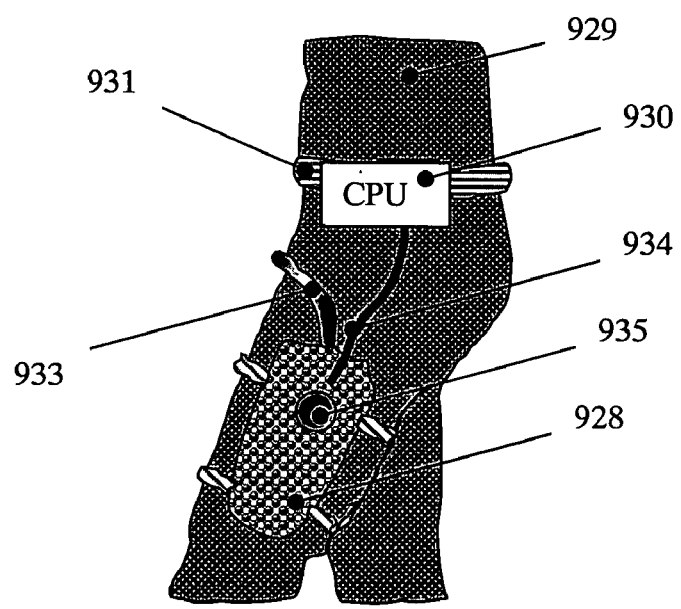

FIGS. 62 and 63 are schematic illustrations of additional possible variations. Urinary bag 928 can be attached to the leg of the patient 929, while CPU 930 with battery is attached to the belt 931. Piezo resonator of SAW 932 may be attached to the connecting tube 933 and electrical signal may be applied through cable 934 from CPU 930, as is shown in FIG. 62. Another embodiment has the additional SAW resonator 935 attached or integrated to urinary bag 928.

Figure 64:
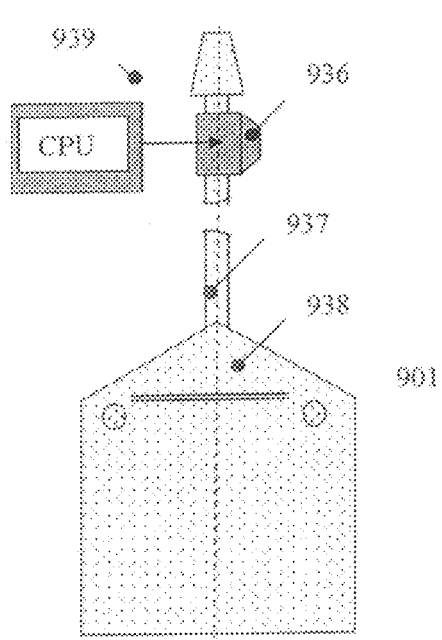
FIG. 64 illustrates additional possible variations of SAW resonator attachment to the collecting tube of urinary bag.
Figure 66:
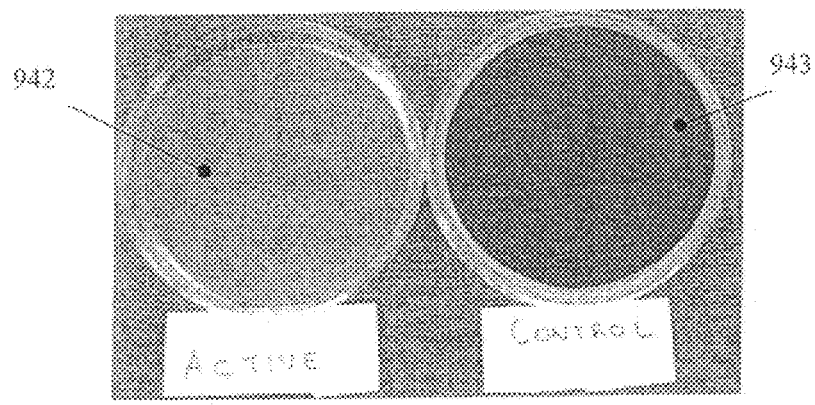
FIG. 66 illustrates experimental results with urinary bag.

FIGS. 64 and 66 illustrate additional possible variations. FIG. 64 shows SAW resonator 936 (may be Uroshield type, described above) attached to collecting tube 937 of urinary bag 938. CPU 939 transmits electrical signals to piezo element 936 (may be one or more) and they generate vibrations. This results in a biofilm prevention process both in the urinary catheter system and urine collection bag.

Figure 65:
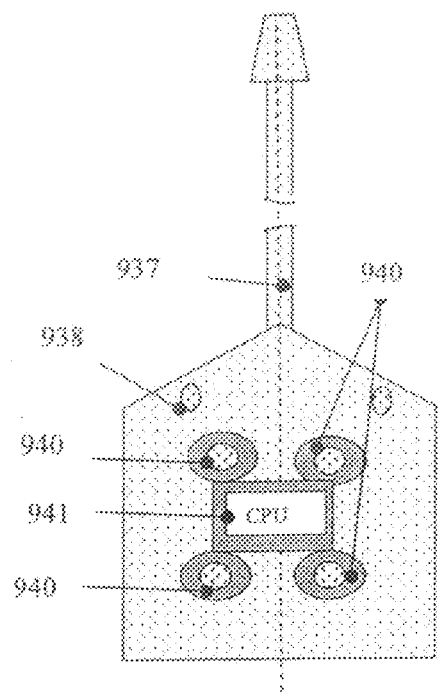
FIG. 65 schematically illustrates another application wherein one or more piezo resonators with CPU are attached to the urinary bag.

FIG. 65 schematically illustrates another application, when one or more piezo resonators 940 with CPU 941 are attached to the urinary bag 938. Multiple thin piezo elements 940 may be placed on the wall of urinary bag 938 (optionally on one or two opposite walls). In this case opposite nano vibration waves may be generated and two separate acoustic processes occur: SAW generation, while the piezo element is attached on one wall; and a standing waves process in collected urine, while two piezo elements are attached on the opposite walls. The first process enables biofilm formation to be prevented; the second process enables killing of bacteria in the urine. These two are placed in opposite manner one relative to another thin piezo element, with low energy applied, may generate standing acoustic waves featuring high dynamic pressure (cavitation process). There has been recently shown that free swimming bacteria can somehow coordinate their motion in fluid-coordination of mass movement of the community. Nanovibration processing by transmitting elastic waves to fluids disorganizes the coordinated movement of the community. The result is a slowdown of the organized communities action.

FIG. 66 illustrates experimental results with a urinary bag. Fluid container with minimal growth media and $10^4$/ml bacteria contamination (*Pseudomonas Aeuriginosa*) were cultivated at 37° C. for 12 days. The container with actuator attached indicates the use of SAW process. The fluid in this container with actuator was clean, the control was murky. Laboratory results show a 2 log reduction compared to the control (bacteria contamination in the activated container was $10^6$/ml but $10^8$/ml in the control). The photos show clear fluid from the container 942 with thin piezo actuators. The fluid in the control container 943 was not transparent due to fermentation of the media by the bacteria.

Our technology enables prevention of biofilm formation at any part of the system, which can be furnished with actuators. Body tissues which are in contact with the activated medical device are protected. In this way, arteries, veins, mucosal membranes and other organs and body cavities are protected from colonization with bacteria and formation of biofilms. Furthermore, if SAW process is generated on indwelling medical device, this process may be further transmitted to the arteries, veins, urinary tract and other body cavities where the device was introduced.

This further transmission of SAW may have positive impact on problematic points in a patient's body.

All aforementioned descriptions and embodiments are not to be considered as restricted to use in medical devices. It will be clear to those skilled in the art that SAW on devices of the present invention can be incorporated or embedded or integrated with any future medical design or accessories.

What is claimed is:

1. A method for inhibiting biofilm formation associated with an indwelling medical device, the indwelling medical device comprising a piezo plate resonator with thickness polarization, the method comprising connecting the piezo plate resonator to an energy source for exciting the piezo plate resonator, controlling the energy source by a central processor unit for generating electrical signals which are transformed by the piezo plate resonator into mechanical vibrations and forming via the piezo plate resonator surface acoustic waves having nanometer amplitudes (nanovibration coating); the piezo plate oscillating at a main frequency and in second and higher harmonic frequencies within a frequency range from 0.02 to 50 MHz thereby creating over surfaces of the indwelling medical device mechanical vibration energy effective in inhibiting bacterial attachment to the indwelling medical device and consequently entry of microorganisms into a human body, and wherein the piezo plate resonator is operative to sense a magnitude of biofilm on the surfaces of the indwelling medical device.

2. The method according to claim 1 wherein the surface acoustic waves propagate throughout all surfaces of the indwelling medical device.

3. The method according to claim 1 wherein amplitude of the surface acoustic waves range from about 1 to about 50 nanometers.

4. The method according to claim 1 wherein the second and higher harmonic frequencies of the surface acoustic waves range from 0.02 to 1.0 MHz.

5. The method according to claim 1 wherein the piezo plate resonator is a piezo ceramic resonator.

6. The method according to claim 5 wherein the piezo ceramic resonator is coupled to the indwelling medical device through an adhesive layer.

7. The method according to claim 1 wherein the energy source is an electro-mechanical energy source.

8. The method according to claim 1 wherein the energy source is an electro-magnetical energy source.

9. The method according to claim 1 wherein the indwelling medical device is a catheter.

10. The method according to claim 1 wherein said piezo plate resonator generates said surface acoustic waves in a longitudinal vibration mode whereby said surface acoustic waves are confined to external surfaces of the indwelling medical device.

11. The method according to claim 1 wherein said piezo plate resonator resonates in a thickness vibration mode whereby the surface acoustic waves are confined to internal surfaces of the indwelling medical device.

12. The method according to claim 1 wherein said piezo plate resonator resonates in a bending vibration mode whereby said surface acoustic waves are produced both on internal and external surfaces of the indwelling medical device.

13. The method according to claim 12 wherein said bending vibration mode has a period corresponding to a wavelength of the surface acoustic waves on the indwelling medical device.

14. The method according to claim 1 wherein said piezo plate resonator resonates in vibration modes which are selected from the group consisting of thickness, longitudinal, and bending modes and combination modes thereof.

15. The method according to claim 1 wherein the piezo plate resonator comprises a bimorph element, comprising a piezo ceramic layer and a metal layer.

16. The method according to claim 15 wherein the piezo ceramic layer and the metal layer have surface areas which are in a respective ratio of about 0.95 to about 1.35.

17. The method according to claim 15 wherein the piezo plate resonator is connected to electrodes, the electrodes being located outside of a central area of said bimorph element thereby achieving stability of second and higher harmonic frequencies produced in the piezo plate resonator.

18. The method according to claim 1 wherein said piezo plate resonator is operative to adjust mechanical vibration energy delivered to said indwelling medical device in response to the magnitude of the biofilm sensed by said resonator.

19. The method according to claim 1 wherein the indwelling medical device is a catheter having a hub or connector and the piezo plate resonator is attached to a hub or connector.

20. The method according to claim 1 wherein the piezo plate resonator comprises a plurality of electrodes for selectively varying modes of vibrations generated by the piezo plate resonator.

21. The method according to claim 1 wherein the indwelling medical device is selected from the group consisting of an Intra Venous catheter, a urinary catheter, a gastric catheter, a lung catheter, a cardiovascular catheter and an endothrahial ventilation tube.

22. An apparatus for inhibiting biofilm formation on surfaces of an indwelling medical device comprising a piezo plate resonator oscillating at a main frequency and in second and higher harmonic frequencies within a frequency range from 0.02 to 50 MHz and being operative to generate surface acoustic waves over surfaces of the medical device to thereby inhibit bacterial attachment to the surfaces, and wherein the apparatus further comprises means for detecting a magnitude of any biofilm formation on surfaces of the indwelling medical device and adjusting oscillations of the surface acoustic waves generated by the piezo plate resonator in response to the magnitude of the biofilm formation.

23. The apparatus according to claim 22 wherein the surface acoustic waves have amplitudes ranging from about 1 to about 50 nanometers.

24. The apparatus according to claim 23 wherein the surface acoustic waves have frequencies ranging from 0.02 to 1.0 MHz.

25. The apparatus according to claim 22 wherein the piezo plate resonator comprises a bimorph element comprising a piezo ceramic layer and a metal layer.

26. The apparatus according to claim 25 wherein surface areas of the piezo ceramic layer to surface areas of the metal layer are in the ratio of about 0.95 to about 1.35.

27. The apparatus according to claim 22 wherein the indwelling medical device comprises a hub or connector and the piezo plate resonator is attached to the hub or connector.

28. The apparatus according to claim 22 wherein said piezo plate resonator comprises a piezo ceramic plate.

29. The apparatus according to claim 28 wherein the piezo ceramic plate has a shape selected from the group consisting of circular, rectangular, ring and disk shapes.

* * * * *